United States Patent
Shell et al.

(10) Patent No.: US 11,829,970 B2
(45) Date of Patent: Nov. 28, 2023

(54) SYSTEM AND METHOD FOR PROVIDING A DISCRETE WORKSPACE

(71) Applicant: Talkbox, LLC, Boulder, CO (US)

(72) Inventors: Michael Ross Shell, Niwot, CO (US); Shamus Hogan, Tucson, AZ (US)

(73) Assignee: Talkbox, LLC, Boulder, CO (US)

( * ) Notice: Subject to any disclaimer, the term of this patent is extended or adjusted under 35 U.S.C. 154(b) by 56 days.

(21) Appl. No.: 17/507,118

(22) Filed: Oct. 21, 2021

(65) Prior Publication Data

US 2022/0180339 A1 Jun. 9, 2022

Related U.S. Application Data

(63) Continuation of application No. 16/851,658, filed on Apr. 17, 2020, now abandoned, which is a continuation-in-part of application No. 16/215,191, filed on Dec. 10, 2018, now abandoned.

(Continued)

(51) Int. Cl.
*G06Q 20/12* (2012.01)
*G08B 13/22* (2006.01)
(Continued)

(52) U.S. Cl.
CPC .............. *G06Q 20/127* (2013.01); *A61L 2/10* (2013.01); *A61L 2/18* (2013.01); *A61L 2/20* (2013.01);
(Continued)

(58) Field of Classification Search
CPC ...... G06Q 10/02; G06Q 10/025; G06Q 50/30; G06Q 30/04; G06Q 20/127; G06Q 20/108;
(Continued)

(56) References Cited

U.S. PATENT DOCUMENTS 3,959,607 A 5/1976 Vargo
6,182,404 B1 2/2001 Rinklake
(Continued)

FOREIGN PATENT DOCUMENTS

WO 2016118797 A1 7/2016

OTHER PUBLICATIONS

International Search Report and Written Opinion from related PCT/US18/64766, dated Feb. 26, 2019. 9 pages.
(Continued)

*Primary Examiner* — Anh Nguyen
(74) *Attorney, Agent, or Firm* — FisherBroyles LLP; Ian R. Walsworth

(57) ABSTRACT

This application describes systems and methods for locating, securing, accessing and utilizing a discrete enclosure or workspace. The discrete enclosure or workspace may be located in a public, private or semi-private setting and may comprise a combination of working platforms or surfaces, seats, desks and other apparatus, as well as computer hardware and software. Systems may comprise natural language processing, artificial intelligence, machine learning and other adaptive learning capabilities to enhance the use of the discrete workspace. The workspace may be dimensioned to be used for a wide variety of activities by one or more users.

14 Claims, 19 Drawing Sheets

Related U.S. Application Data

(60) Provisional application No. 62/596,675, filed on Dec. 8, 2017.

(51) Int. Cl.

| | | |
|---|---|---|
| *G07C 9/30* | (2020.01) | |
| *G16H 40/67* | (2018.01) | |
| *G06Q 50/26* | (2012.01) | |
| *G06Q 20/10* | (2012.01) | |
| *E04H 1/12* | (2006.01) | |
| *C12Q 1/06* | (2006.01) | |
| *A61L 2/28* | (2006.01) | |
| *A61L 2/24* | (2006.01) | |
| *A61L 2/18* | (2006.01) | |
| *A61L 2/10* | (2006.01) | |
| *A61L 2/20* | (2006.01) | |
| *G08B 3/10* | (2006.01) | |
| *G08B 7/06* | (2006.01) | |
| *G06Q 10/02* | (2012.01) | |

(52) U.S. Cl.
CPC .................... *A61L 2/24* (2013.01); *A61L 2/28* (2013.01); *C12Q 1/06* (2013.01); *E04H 1/125* (2013.01); *G06Q 10/02* (2013.01); *G06Q 20/108* (2013.01); *G06Q 50/265* (2013.01); *G07C 9/30* (2020.01); *G08B 3/1008* (2013.01); *G08B 7/06* (2013.01); *G08B 13/22* (2013.01); *G16H 40/67* (2018.01)

(58) Field of Classification Search
CPC ... G06Q 50/265; G06F 17/3053; G10L 25/18; H04L 47/827; E04H 1/06; E04H 1/125; E04H 1/14; G05B 13/02; A61L 2/10; A61L 2/18; A61L 2/20; A61L 2/24; A61L 2/28; A61L 2202/14; A61L 2202/25; A61L 2209/111; A61L 2/22; A61L 9/14; A61L 9/20; A61L 2202/17; C12Q 1/06; G07C 9/30; G08B 3/1008; G08B 7/06; G08B 13/22; G16H 40/67; G07F 19/205; G07F 19/207
USPC ...................... 52/173.1, 741.1, 79.1; 709/205
See application file for complete search history.

(56) References Cited

U.S. PATENT DOCUMENTS

| | | | |
|---|---|---|---|
| 6,475,357 B2 | 11/2002 | Lakshmikanthan | |
| 10,107,708 B1 | 10/2018 | Schick | |
| 2002/0065583 A1 | 5/2002 | Okada | |
| 2002/0163720 A1 | 11/2002 | Piepel | |
| 2005/0088693 A1 | 4/2005 | Schnoebelen | |
| 2007/0136133 A1 | 6/2007 | Li | |
| 2008/0031770 A1* | 2/2008 | Heselton | C01B 13/11 422/4 |
| 2008/0055101 A1* | 3/2008 | Chung | G08B 13/19608 348/42 |
| 2008/0072509 A1 | 3/2008 | Eberhardt | |
| 2009/0289775 A1* | 11/2009 | Kubota | G06Q 10/087 340/10.6 |
| 2010/0042555 A1 | 2/2010 | Ranen et al. | |
| 2011/0081273 A1* | 4/2011 | Sunderland | A61L 9/22 422/108 |
| 2012/0305340 A1 | 12/2012 | Wu | |
| 2013/0067834 A1 | 3/2013 | Downey et al. | |
| 2013/0183749 A1* | 7/2013 | Aamodt | A61L 2/22 435/287.1 |
| 2013/0226444 A1 | 8/2013 | Johansson | |
| 2014/0077929 A1* | 3/2014 | Dumas | G07C 9/00571 340/5.61 |
| 2014/0157619 A1 | 6/2014 | Cookson et al. | |
| 2015/0114763 A1* | 4/2015 | Kim | B66B 5/0012 187/392 |
| 2015/0156031 A1* | 6/2015 | Fadell | G08B 27/003 700/90 |
| 2015/0193739 A1 | 7/2015 | Min et al. | |
| 2015/0204551 A1 | 7/2015 | Nair | |
| 2015/0258234 A1* | 9/2015 | Larsen | A61L 9/04 422/4 |
| 2015/0267404 A1 | 9/2015 | Yau | |
| 2015/0332564 A1 | 11/2015 | Weinberg | |
| 2016/0027029 A1 | 1/2016 | Poole | |
| 2016/0117688 A1 | 4/2016 | Ghosh | |
| 2016/0162830 A1 | 6/2016 | Devaiah | |
| 2016/0220716 A1* | 8/2016 | Childress | B64D 11/02 |
| 2016/0285785 A1 | 9/2016 | Thye | |
| 2016/0125468 A1 | 10/2016 | Staneluis | |
| 2017/0132909 A1 | 5/2017 | Rabb et al. | |
| 2017/0265046 A1 | 9/2017 | Chen | |
| 2017/0289494 A1 | 10/2017 | Garing | |
| 2018/0012475 A1 | 1/2018 | Hsu | |
| 2018/0116553 A1* | 5/2018 | Ten Kate | A61B 5/083 |
| 2018/0174076 A1 | 6/2018 | Fukami | |
| 2018/0199743 A1 | 7/2018 | Kajak | |
| 2019/0006047 A1 | 1/2019 | Gorek | |
| 2019/0080097 A1 | 3/2019 | Hardee | |
| 2019/0130315 A1 | 5/2019 | Tokuchi | |
| 2019/0167829 A1* | 6/2019 | Grinstead | A61L 2/085 |
| 2020/0048933 A1 | 2/2020 | Li | |
| 2020/0102779 A1* | 4/2020 | Rabinowitz | E05F 15/624 |
| 2020/0237946 A1* | 7/2020 | Shell | A61L 2/28 |

OTHER PUBLICATIONS

International Preliminary Report on Patentability from related PCT/US18/64766, dated Jun. 18, 2020. 7 pages.
Framery—The Pioneering Office Booths. https://www.frameryacoustics.com/en/. Believed active since Jun. 2018.
Spacio Meeting Pods. https://spaciomeetingpods.com/spacio-meeting-pods/. Believed active since Mar. 2019.
Zenbooth. https://zenbooth.net/. Believed active since Aug. 2018.
Spaceworx Decible Acoustic Phone Booth. http://spaceworx.us/office-phone-booth/. Believed active since Jul. 2018.
Cubicall Phone Booths. https://www.cubicallbooth.com/. Believed active since Sep. 2017.
OfficeBricks. https://officebricks.de/?lang=en. Believed active since Oct. 2016.
Airea pods. https://www.orangebox.com/products/Airea.
Fantoni Acoustic Room. http://www.fantoni.it/en/home/sistemi-ufficio/Meeting/ACOUSTIC-ROOM.html.
FremGroup—Oasis Collection. https://www.frem.co.ukffiem-products/collaborative/oasis-collection/oasis-linear.
Abbrrbox. https://www.jabbrrbox.comt Believed active since Feb. 2017.
Mamava. https://www.mamava.com/. Believed active since Jun. 2013.
StudioShed. https://www.studio-shed.com/. Believed active since May 2009.
Non-Final Office Action from parent U.S. Appl. No. 16/215,191, dated Jul. 9, 2021.
Final Office Action from parent U.S. Appl. No. 16/215,191, dated Sep. 23, 2020.
Non-Final Office Action from parent U.S. Appl. No. 16/215,191, dated Mar. 31, 2020.
Non-Final Office Action from parent U.S. Appl. No. 16/851,658, dated Oct. 29, 2020.
Final Office Action from parent U.S. Appl. No. 16/851,658, dated Apr. 21, 2021.

* cited by examiner

SYSTEM AND METHOD FOR PROVIDING A DISCRETE WORKSPACE

CROSS-REFERENCE TO RELATED APPLICATIONS

This application is a Continuation of U.S. patent application Ser. No. 16/851,658, filed Apr. 17, 2020, which is a Continuation-In-Part of U.S. patent application Ser. No. 16/215,191, filed Dec. 10, 2018, which claims priority to and the benefit under 35 U.S.C. § 119(e) to U.S. Provisional Patent Application Ser. No. 62/596,675, filed Dec. 8, 2017, the contents of which are incorporated by reference in their entirety.

FIELD OF THE INVENTION

The present disclosure is generally directed toward systems and methods for providing workspace services to users in public, private or semi-private settings. More specifically, this disclosure relates to a workspace enclosure that facilitates a number of user services, as well as a system and method for locating, reserving, accessing and using the same.

BACKGROUND

Public venues, such as airports, train stations, sporting events generally fail to provide private or semi-private secure locations for patrons to use to relax, make telephone calls, conduct business, compose and mail letters, scan or retrieve documents, and even sleep while a person is in transit or during long delays. There is presently no system or method in a public venue that provides privacy, quiet space, communication, and entertainment services for a user, particularly for a pre-determined and pre-specified period of time by the user. Similar shortcomings in the art exist for private workspaces, libraries, workshare locations, hotel lobbies, conference centers, etc. Often the generally open architecture and floorplan of many such spaces makes it difficult, if not impossible, to conduct private and uninterrupted business.

In addition to these shortcomings, there is presently no system or method which provides a private and internal environment that is completely customizable by the user, and which caters to each user's unique needs. For example, private or semi-private workspaces would be enhanced by providing services to the user, such as delivery services (both to and from a workspace), printing/copying services, document certification services, secure data transmission, currency exchange, translation services and other services. In certain cases, the location of a user in a secure workspace would facilitate the provision of these services from service providers located in the vicinity of the workspace and arranged by a user of the systems and methods described herein.

Furthermore, there are no systems or methods for permitting a user to utilize the services described above in which such workspaces are easily moveable, can be modularized and or expanded quickly and efficiently, and be provided to one or more individuals at a time. It is with respect to the above issues and other problems presently faced by those of skill in the pertinent art that the embodiments presented herein were contemplated. The present invention solves the problems associated with the prior art and provides an apparatus and method that incorporates a custom client-server application, a host of environmental sensors with automatic, event-based triggers, and a rugged exterior that is also easily movable and where applicable, self-powering. Other advantages and benefits will become apparent after reviewing the Summary and Detailed Description sections below.

SUMMARY OF THE INVENTION

Accordingly, the present disclosure relates to systems and methods that overcome the problems identified above. While several advantages of the system and method of one embodiment are provided in this section, this Summary is neither intended nor should it be construed as being representative of the full extent and scope of the present invention. The present invention is set forth in various levels of detail in the Summary as well as in the attached drawings and in the Detailed Description, and no limitation as to the scope of this disclosure is intended by either the inclusion or non-inclusion of elements, components, etc. in the Summary. Additional aspects of the present disclosure will become more readily apparent from the materials included in the Detailed Description below.

In view of the shortcomings in the prior art, it is one aspect of the present disclosure to provide a user with a system ("Smartbooth") for locating, securing, accessing and utilizing a discrete enclosure or workspace. In embodiments, the enclosure may comprise a combination of working platforms or surfaces, seats, desks and other apparatus. The enclosure may contain a number of pieces of equipment, including but not limited to computers (PCs), tablets, screens, copying/imaging equipment, WiFi connectivity, electrical outlets, printers, facsimile machines, telephone(s), virtual reality components (such as a headset, visors, gloves, and CPU), hardware components and sensors. In one preferred embodiment, computer hardware (including, for example, an internal or external laptop, tablet and/or other personal computing device) may be installed with software applications to manage features and functions within the Smartbooth, or alternatively to arrange for additional services provided in connection with the Smartbooth.

Additionally, the Smartbooth may comprise one or more data repositories and or secure data servers, which in turn may provide a hub to input and output data, files, and media to ancillary devices that enable provisioning of services. In embodiments, in addition to the software applications identified above, a mobile application is available for use in payment, booking/scheduling and selection of features available in a particular Smartbooth.

It is yet another aspect to provide a user with a system that manages a number of functions. These functions may include, by way of example but not limitation: dynamically pricing blocks of time for use of a particular Smartbooth, which may be based on a pricing algorithm; collecting and validating of payment for use of the Smartbooth; locating, determining availability, booking and reserving blocks of time to use one or more services associated with the Smartbooth; controlling access to the Smartbooth; serving and trafficking of media and advertisements and displays inside or on the exterior of the Smartbooth; speakers located within or adjacent the Smartbooth; automating hardware behaviors such as lighting, sounds, door lock, and playing media within or adjacent the Smartbooth; consuming and transmitting data from environmental observation hardware including video cameras, microphones, and sensors of various types such as light, pressure, laser, audio, and environmental sensors; connecting to the internet or a private network; connecting and interfacing with the Smartbooth Backend to relay data, audio and video; receiving, displaying and broadcasting public announcements including but not limited to weather, safety and emergency-related information and alerts; managing integrations and entitlements with third party services integrated into the Smartbooth; and other functions described herein.

The present disclosure according to embodiments further comprises a method to reserve, locate, access and use the Smartbooth. In one embodiment, a user pays for a session in the Smartbooth outside the booth. The user then enters the Smartbooth after payment has been accepted, and the user's presence inside the booth is detected by the sensors inside the Smartbooth. Audio may be played through the Smartbooth speakers to welcome a user to the Smartbooth session. Alternatively, a visual welcome may be provided via a display associated with the Smartbooth. Throughout the session, the remaining purchased time may be displayed on the inside (and in some instances, outside) of the booth, and Smartbooth displays may also alert a user when the purchased time has run out. At the end of the user's session in the Smartbooth, audio is played through speakers (or through a visual display) that prompts the user to exit the booth or pay to extend the session.

In other embodiments, if a user enters the Smartbooth without making a payment, the user's presence inside the Smartbooth is detected, and audio is played through speakers (or a display) inside the Smartbooth that prompts the user to exit the booth or to make a payment.

It is to be expressly understood that the ensuing description provides embodiments only, and is not intended to limit the scope, applicability, or configuration of the invention. Rather, this Summary will provide those skilled in the art with an enabling description for implementing the embodiments. It should be understood that various changes may be made in the function and arrangement of elements without departing from the spirit and scope of the appended claims. Furthermore, while embodiments of the present disclosure will be described in connection with various examples, it should be appreciated that embodiments of the present disclosure are not intended to be limited in any way.

While the invention is described in terms of exemplary embodiments, it should be appreciated that individual aspects of the invention may be separately claimed.

BRIEF DESCRIPTION OF THE DRAWINGS

Those of skill in the art will recognize that the following description is merely illustrative of the principles of the disclosure, which may be applied in various ways to provide many different alternative embodiments. This description is made for illustrating the general principles of this disclosure and is not meant to limit the inventive concepts herein.

The accompanying drawings, which are incorporated in and constitute a part of the specification, illustrate particular examples or embodiments of the disclosure. These drawings, taken together with the general description of the disclosure provided above and the detailed description provided below, serve to explain the principles of the disclosure. In the drawings.

Figure 1:
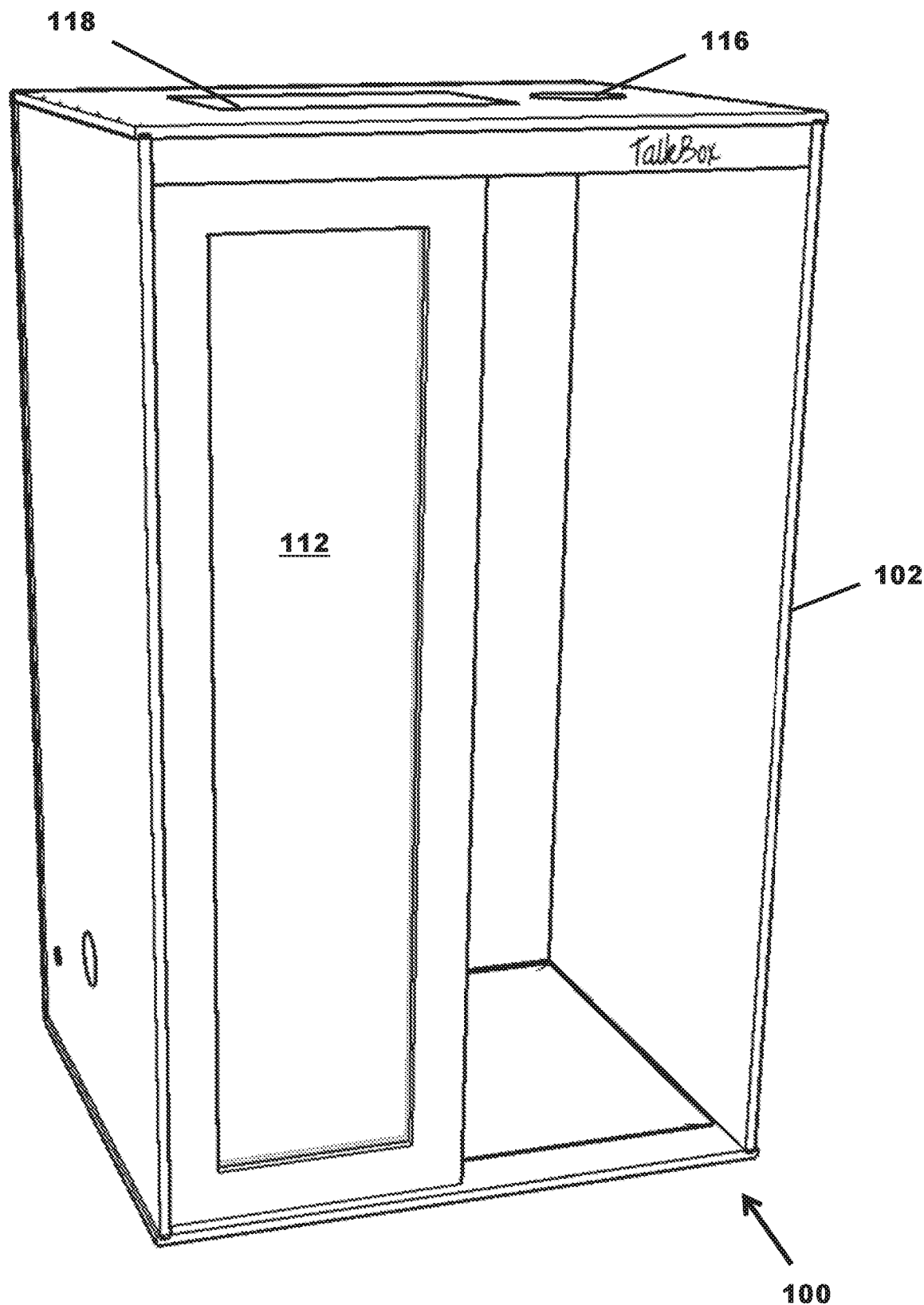
FIG. 1 is a perspective view of the system according to embodiments.

It should be understood that the drawings are not necessarily to scale. In certain instances, details that are not necessary for an understanding of the disclosure or that render other details difficult to perceive may have been omitted. It should be understood, of course, that the disclosure is not necessarily limited to the particular embodiments illustrated herein.

DETAILED DESCRIPTION

The present invention provides benefits across a broad spectrum of endeavors. It is applicant's intent that this specification and the claims appended hereto be accorded a breadth in keeping with the scope and spirit of the invention being disclosed despite what might appear to be limiting language imposed by the requirements of referring to the specific examples disclosed. Thus, to acquaint persons skilled in the pertinent arts most closely related to the present invention, a preferred embodiment of the system is disclosed for the purpose of illustrating the nature of the invention. An exemplary method of installing, assembling and operating the system is described in detail according to a preferred embodiment, without attempting to describe all of the various forms and modifications in which the invention might be embodied. As such, the embodiments described herein are illustrative, and, as will become apparent to those skilled in the art, can be modified in numerous ways within the scope and spirit of the disclosure.

Although the following text sets forth a detailed description of numerous different embodiments, it should be understood that the legal scope of the invention is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

Certain terms are used throughout the following description to refer to particular system components. As one skilled in the art will appreciate, a person may refer to a component by different names. This document does not intend to distinguish between components that differ in name but not function. In the following disclosure and in the claims, the terms "including" and "comprising" are used in an open-ended fashion, and thus should be interpreted to mean "including, but not limited to . . . " Also, the term "couple" or "couples" is intended to mean either an indirect or direct connection. When used in a mechanical context, if a first component couples or is coupled to a second component, the connection between the components may be through a direct engagement of the two components, or through an indirect connection that is accomplished via other intermediate components, devices and/or connections. In addition, when used in an electrical context, if a first device couples to a second device, that connection may be through a direct electrical connection, or through an indirect electrical connection via other devices and connections. Connections can occur in a unidirectional, bidirectional or variable directional manner over all known means of network connectivity.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this disclosure is referred to in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. § 112, subparagraph (f).

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The terms "automated", "automatically", "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "machine-readable media" as used herein refers to any tangible storage that participates in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a flexible disk, hard disk, magnetic tape, or any other magnetic medium, magneto-optical medium, a CD-ROM, any other optical medium, a RAM, a PROM, an EPROM, a FLASH-EPROM, a solid state medium like a memory card, any other memory chip or cartridge, or any other medium from which a computer or like machine can read. When the computer-readable media is configured as a database, it is to be understood that the database may be any type of database, such as relational, hierarchical, object-oriented, and/or the like. Accordingly, the invention is considered to include a tangible storage medium and prior art-recognized equivalents and successor media, in which the software implementations of the present invention are stored.

The terms "determine", "calculate", and "compute," and variations thereof, as used herein, are used interchangeably and include any type of methodology, process, mathematical operation or technique.

The term "module" as used herein refers to any known or later developed hardware, software, firmware, machine engine, artificial intelligence, fuzzy logic, or combination of hardware and software that is capable of performing the functionality associated with that element.

System Enclosures & Hardware

Referring now to the drawings, FIGS. 1-12C depict varying embodiments of a system 100, which preferably comprises an enclosed structure, ("Talkbox" or "Smartbooth") 102. These embodiments provide one or more users with a private or semi-private internal environment that is customizable to a user's individual needs. The Smartbooth 102 can also provide multiple users a public, private or semi-private internal environment, as described above, which is further described in greater detail below. In certain embodiments, the Smartbooth may be located in a public setting (such as an airport terminal or concourse, commuter station, lobby, conference center, intersection, bus stop, library, museum, etc.), but provide a private workspace for a user. In other embodiments, the Smartbooth may be located in a private or semi-private setting (such as an office or other typical working environment) and provide the same functions as with a public setting.

In one preferred embodiment, the system 100 may comprise one or more Smartbooths, such as the exemplary Smartbooth 102 shown in FIGS. 1-6. The Smartbooth 102 preferably comprises a modular enclosure, such as the enclosure shown in FIG. 1. Despite its modular nature, the Smartbooth 102 may comprise certain components, including computer hardware (i.e., a tablet or PCs), installed inside or about the structure of the Smartbooth 102. The computer hardware may contain one or more software applications, and manage a number of features and functions that as a whole enable services provided by the Smartbooth 102 to a user. Additionally, the computer hardware and applications inside the enclosure of the Smartbooth 102 may further comprise a physical hub or virtual connectivity for a user to input and output data. Data may be comprised of files, documents and other machine-readable media, and input of data by the user may facilitate connectivity to ancillary devices that enable provisioning of services.

Still referring to FIGS. 1-6, the Smartbooth 102 may comprise adequate space for a single user to work, rest or engage in other activities while using the Smartbooth 102. The Smartbooth 102 is preferably comprised of a work surface 122, lighting elements 118 and other environmental features to promote the activities of the user. For example, the Smartbooth 102 may comprise ventilation (described in greater detail in relation to FIGS. 7-10B) to promote temperature and air control within the Smartbooth 102. The Smartbooth 102 may comprise one or more lighting elements 118 to illuminate the interior of the Smartbooth 102 or specific surfaces within the Smartbooth 102. The Smartbooth 102 may comprise one or more speakers 116 for amplifying sounds (either within the Smartbooth 102 or ambient to the Smartbooth 102) to alert the user of important information and/or to ensure privacy of conversations occurring within the Smartbooth 102.

Figure 2:
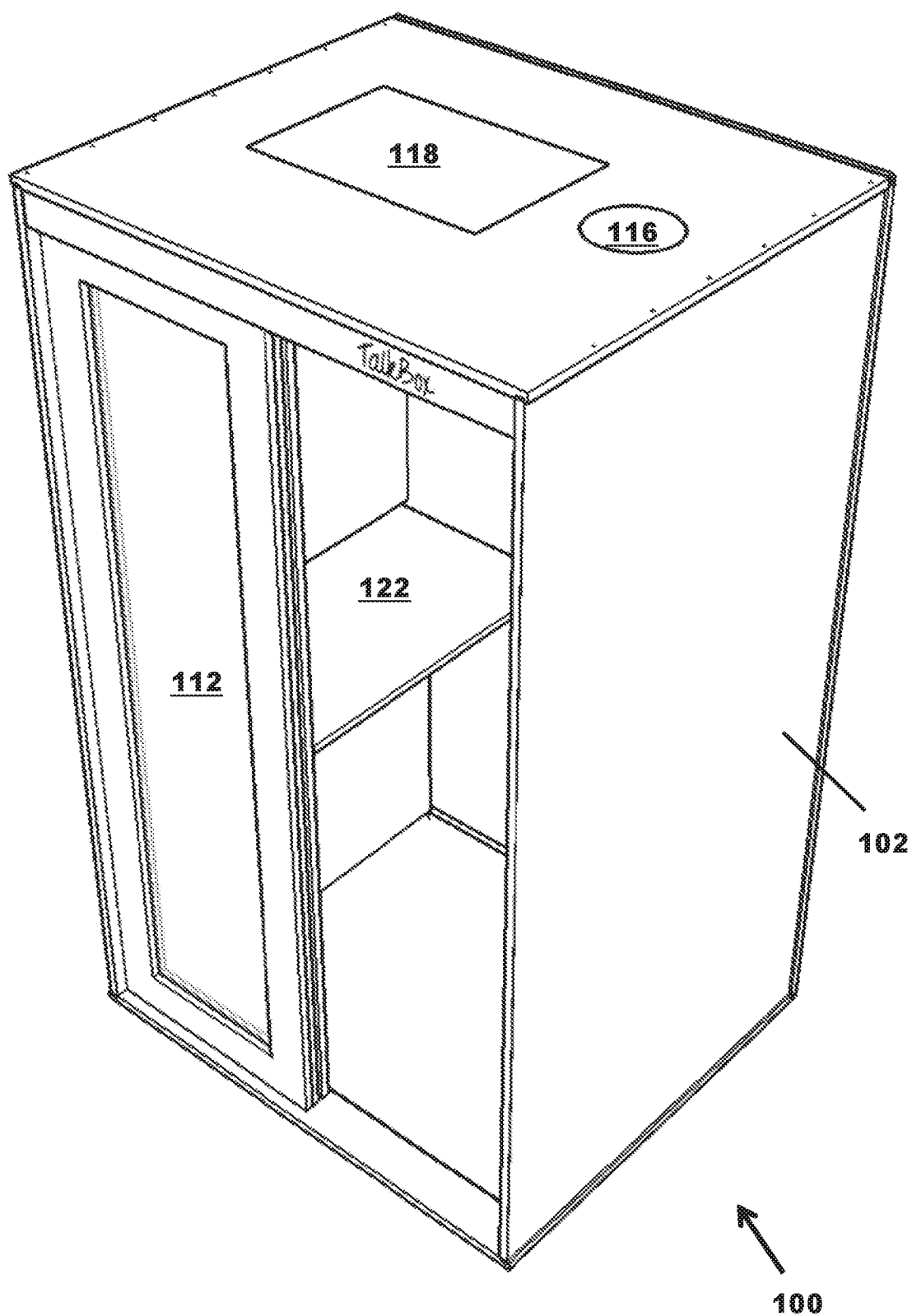
FIG. 2 is another perspective view of the system according to embodiments.
Figure 3:
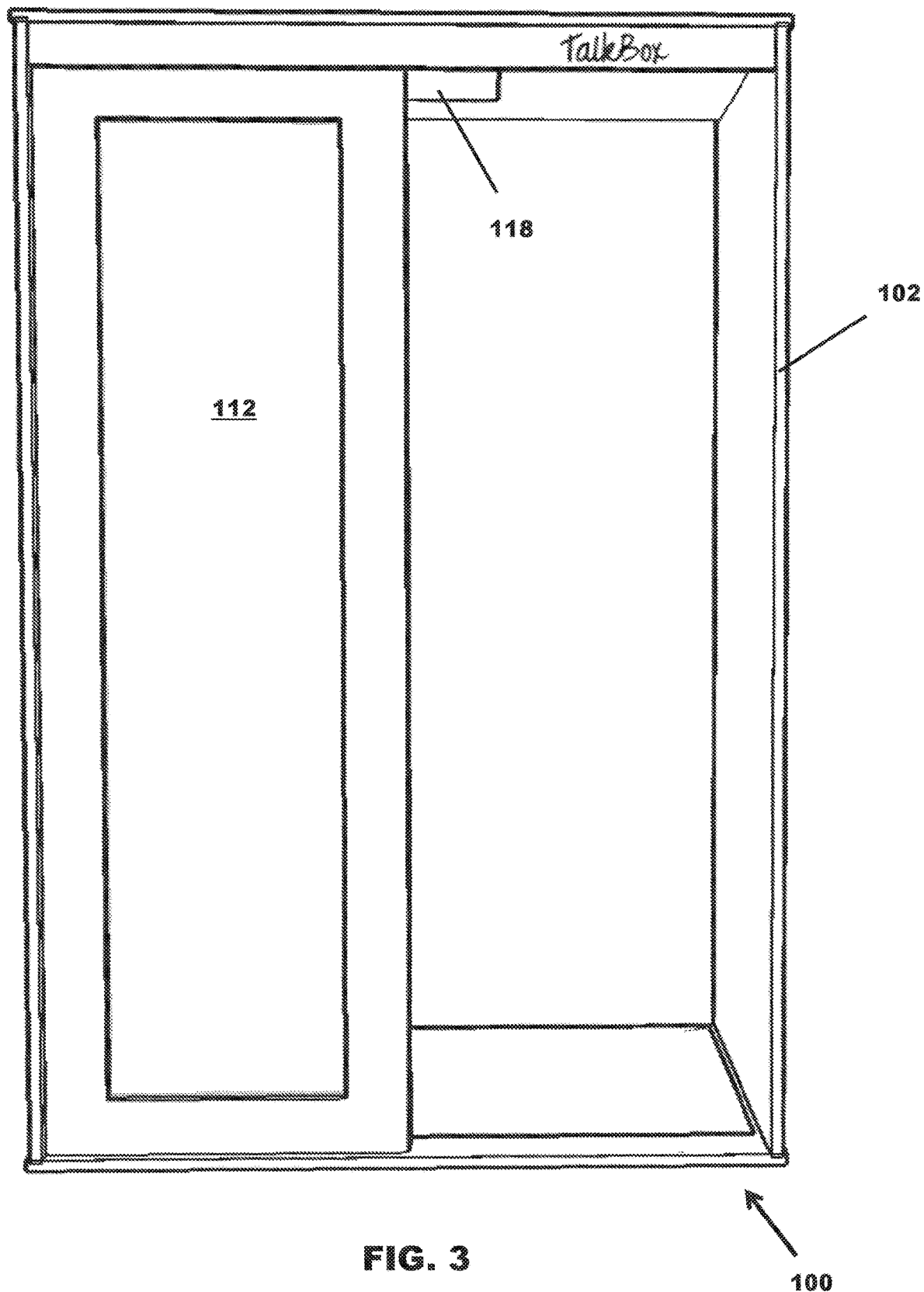
FIG. 3 is a front elevation view of the system according to the embodiment of FIG. 2.
Figure 4:
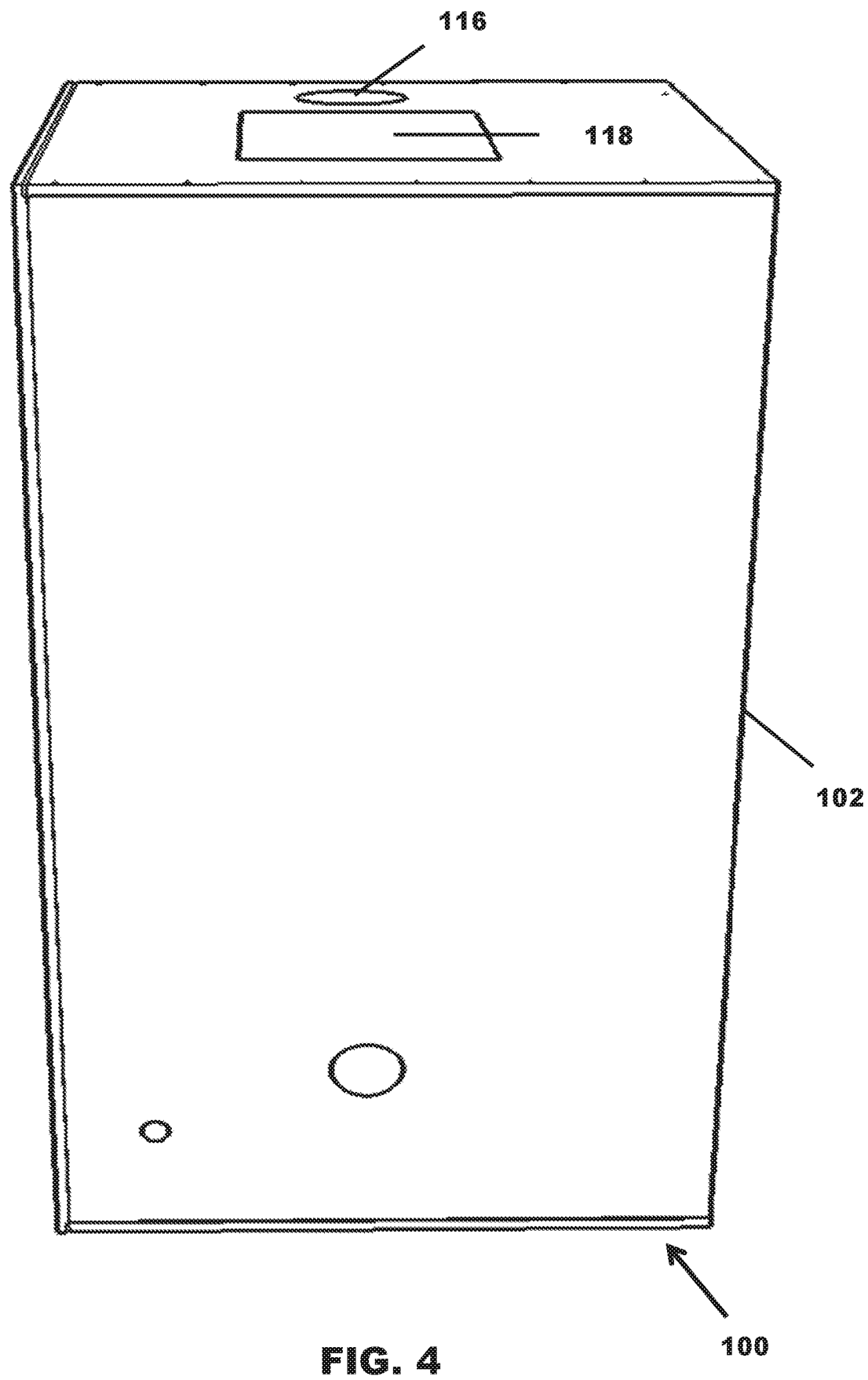
FIG. 4 is a rear perspective view of the system according to the embodiment of FIG. 2.

In embodiments, Smartbooth 102 provides user(s) privacy and security while in use by automatically closing and locking its door 112 after a paid session is initiated and a user's presence is detected. In embodiments, the door's closure 112 may be automatically facilitated by a spool/winch motor, servo-motor, counterweight-assisted pulley, actuating arm, and/or an electromagnetic closure and locking apparatus or equivalent mechanical apparatus. For example, upon closure detection, such as via an electromechanical switch within the door 112 or door frame, an electromagnetic or other lock engages, keeping the Smartbooth 102 closed and locked for the duration of a unique session. A user may end a session and exit the Smartbooth 102 at any time prior to expiration of the session. Upon the completion of a paid session, Smartbooth 102 automatically reverses the close-and-lock procedure to a default, normally-open state. Once an electromagnetic lock engages, the door 112 may be locked open as shown in FIGS. 1-3.

The Smartbooth 102 is preferably configured to monitor the door 112 transition state between open and closed. Monitoring in these embodiments may be comprised of: (1) accelerometers to track the state of the door being open, closed, or partially opened or closed; (2) electromagnetic sensors to close a circuit when the door is closed; (3) pressure sensors to detect the force of a door opening or closing; or (4) distance measurement methods of rods, cords, or the length of the door itself to estimate the state of closure of the door.

The Smartbooth 102 interior may include seating, tables, desks, and other features designed to satisfy ergonomic requirements of the user of the Smartbooth 102, and may be adjustable. The various tables, desks, chairs, sofas, or beds located within a Smartbooth 102 may be adjusted in height, position, orientation, through manual or automatic adjustments. The Smartbooth 102 may be comprised of sound dampening materials for ensuring privacy and avoiding disturbance from noises surrounding the location of the Smartbooth 102.

Additional components may be provided with a Smartbooth 102, including those not shown in FIGS. 1-6. For instance, one or more sensors may be included with a Smartbooth 102 such that, upon the commencement of a new (or termination of a current) paid session, the Smartbooth 102 may be configured to read the input values of sound, light, pressure, temperature, infrared, and humidity sensors. Further description of sensors are provided in connection with FIGS. 11A-12C. In these embodiments, the Smartbooth 102 or the user may configure and adjust internal controls accordingly, including by targeting predetermined set points, which may be adjusted during or between sessions. In such embodiment, controls may be adjusted by the user or an administrator.

In one embodiment, the door 112 is comprised substantially of glass or other transparent or semi-transparent material to allow people outside the Smartbooth 102 to observe that it is occupied or unoccupied by another user. This may be beneficial for another person arranging to meet with a specific user in a Smartbooth 102. For a user desiring more privacy, the glass door may be comprised of smart-glass or equivalent selectively tinted glass. In some embodiments, a Smartbooth 102 may be equipped with smart glass, with variable opacity affected by electrochromic, photochromic, thermochromic, suspended particle, micro-blind and/or polymer dispersed liquid crystal devices. Smart glass opacity settings may be available during paid sessions. In some alternative embodiments, a Smartbooth 102 may also be optionally equipped with thicker bullet-resistant walls, bullet-resistant glass, and hardened locking devices, effectively transforming the Smartbooth into a safe room in the event of an emergency.

In embodiments, internal controls may be provided to adjust light levels within the Smartbooth through, for example, the use of intelligent lighting elements 118 or 'smart lighting'. Smart lighting may comprise individual LEDs (light emitting diodes) that can be adjusted so that individual lights, or a combination of different colored lights across the color spectrum provide a different experience to the user and/or modify the degree the Smartbooth is lit. In some embodiments, a combination of lights may be a single color, such as green, while in other embodiments, a combination of lights may be preset to simulate the colors of 'sunset', 'midday', 'early morning', or other simulations of lighting conditions. Another embodiment of internal controls may be the sounds emanating out of the speaker system within the smart booth. In some cases, the Smartbooth user may specify a type or genre of music (jazz, classical, pop, rock, rap), or may choose a white noise, or a specified radio station found on the AM or FM radio spectrums or via satellite radio services.

In another embodiment, internal controls may be utilized to provide video content that is displayed on a screen or other display associated with the Smartbooth. In some embodiments, the video content may be: a preset station, (such as CNBC); predetermined web sites for display, such as Bloomberg financial data content; or other predetermined static, dynamic, streaming, or interactive content.

Another embodiment comprises the use of internal controls to affect olfactory scents on a predetermined basis, whereby the Smartbooth would emanate smells into the booth per the predetermined preferences of the user, such as different varieties of perfume, potpourri, incense, food or cooking scents, etc. Such scent(s) may be emanated into the Smartbooth through the use of injection of liquid mist into the air that is flowing through the Smartbooth ventilation system, at the appropriate ratios to create a pleasant olfactory experience or negate a negative olfactory experience. The appropriate rations may be determined by computational machinery associated with the Smartbooth and/or applications residing on the computational machinery that takes into consideration the rate of airflow, size of space, and preferences set by the user.

In embodiments, the Smartbooth 102 further comprises a cellular transmitter to provide connections for mobile phones and other devices that use radio technologies to communicate data or analog signals. The collective cellular technologies across multiple Smartbooths 102 may be combined to create mesh networks, whereby signals can be relayed across nodes in the network, in a peer-to-peer fashion. Each individual Smartbooth 102 may also comprise a different node in the network. This proprietary network may continue to operate and/or transfer data between Smartbooths in peer-to-peer fashion without reliance on cellular, WiFi, or other 3rd party network signals. In embodiments, a TalkBox mesh network may connect with 3rd party networks to facilitate connection to the internet, cellular networks, satellites, or other networks that transfer data, communicate via radio waves or other signals. In other embodiments, there may be a 'private' network to which access is granted only to users who are entitled or authorized based on paid access or membership in certain groups entitled to the private service. In other embodiments, a public access network may be made available. The Smartbooth 102 may also incorporate radio base stations, microcells or equivalent components to support different network architectures.

As described above in relation to FIGS. 1-6, the Smartbooth may comprise one or more speakers 116 that are for use by a user, an administrator, or authorities, or a combination of the three. The Smartbooth 102 may also comprise one or more fans or other air circulation apparatus. In embodiments, for the duration of a session, the Smartbooth 102 may continuously monitor and adjust white noise levels (via a decibel meter, for example) and ventilation fan speeds (via temperature and humidity sensors, for example) to maintain predetermined environmental set points. In embodiments, a user may override these predetermined set points via user-controlled adjustments.

In one embodiment, upon the commencement of a paid session, the Smartbooth can positively identify distinct customers who have permitted Smartbooth 102 to read their travel itineraries via third party APIs, such that a virtual concierge service is launched. The virtual concierge enables a user to easily revise elements of their travel itineraries and explore noteworthy attributes of their origin, connecting, and destination travel locations, including weather, news, and a calendar of local events. In one embodiment, in the event the Smartbooth 102 is installed in an airport, users have the option of providing their flight number in order to receive real-time updates and alerts regarding their flight status for the duration of their session. The user may also change itineraries, seat assignment, baggage options, etc. through the Smartbooth 102. This information and automated travel advisories may be provided through the speakers, through displays (i.e., monitors) or other components provided with the Smartbooth 102 and described herein.

As mentioned above, upon detection of an unpaid presence, Smartbooth 102 incrementally adjusts internal and external control and display elements to encourage the commencement of a paid session, via the payment system 110, or alternatively upon the departure of a non-paying customer. Such controls and elements may include noise, visual cues or other indicia to alert the user that they must begin a session to utilize the Smartbooth 102. In other embodiments, the Smartbooth 102 door 112 remains closed until a session is initiated.

In embodiments, the Smartbooth 102 monitors its external surroundings to modulate internal environmental set points as well as return data to the Smartbooth 102 for further analysis and processing. In some embodiments, the Smartbooth assesses external foot traffic to, among other purposes, compute advertising efficiency via laser, light, radio wave, ultrasonic wave, passive infrared, and video analysis sensors and methods, which can then be displayed, for example, on an advertisement screen associated with the Smartbooth.

In some embodiments, Smartbooth 102 continuously monitors power consumption and the potential presence of spilled liquids via desktop drainage channels and embedded sensors. In embodiments, the Smartbooth 102 also captures and returns the following environmental data: temperature, humidity, barometric pressure, wind speed, noise level, brightness, and (via accelerometers and video analytics) system "shock" events requiring immediate attention.

Smartbooth 102 booths are preferably easy to assemble, may be modularized in single or multiple units, can be set up in virtually any location (public, private or semi-private) and can also be moved from location to location. For example, some embodiments come equipped with integrated, in-floor casters that can be deployed by administrators to move the Smartbooth 102 to a new location. Once a new location is selected, the administrator retracts the casters into the Smartbooth floor. In this manner, a Smartbooth 102 may be quickly positioned in a high-traffic or other desirable area in, for example, a public space such as an airport, bus or train terminal, etc.

The Smartbooth 102 may accommodate multiple users. The Smartbooth 102 can be of larger or smaller dimensions and proportions to those shown in FIGS. 1-6, and it is expressly understood that the drawing figures appended hereto are not necessarily to scale. Smartbooth 102 may be reserved for meetings or group activities according to these embodiments.

Regardless of the physical structure and size of the enclosure, the Smartbooth 102 may measurably dampen noise levels on the outside relative to the inside of the Smartbooth 102. Additionally, sound emanating from inside the Smartbooth 102 may be measurably dampened from escaping to the exterior of the Smartbooth 102. In one embodiment, for example, measurement is conducted through the use of decibel meters. Decibel meters may be placed inside and outside of the Smartbooth 102 and may be used to compare noise levels at intervals to determine patterns of sound both escaping the Smartbooth 102 and entering the Smartbooth 102. Based on that data, refinements to sound dampening approaches will be made. Other sound dampening methods known in the art may also be applied. For example, sound dampening methods and techniques may include materials selection, strategic layering and spacing of layers of material, structuring patterns of materials to effectively deflect, scatter, or deaden sound waves.

In certain embodiments, the Smartbooth 102 will also have the ability to lock or unlock the door 112 manually from the interior, including via remote control through the Smartbooth 102, via an app on a mobile device, or by entering a code on a keypad on the exterior of the Smartbooth 102 that will be specific to the customer using the services provided by the Smartbooth 102, in the allotted time purchased by the customer. Some types of locks contemplated for use with the Smartbooth 102 include, but are not limited to, Electromagnetic, Padlocks, Deadbolts, Knob Locks, Lever Handle Locks, Cam Locks, Rim/Mortise Locks, Euro Profile Cylinders, Wall Mounted Locks, Interchangeable Core Cylinders, Furniture Locks, T-Handle Locks, Rim Latch Locks, Electric Drop Bolt, Key In Knob Cylinders, or other types of locking devices known in the art. In one embodiment, the locks 112 are electromagnetically controlled, so that if the circuit to the lock is cut, the lock automatically opens. This avoids the possibility of someone being locked inside the Smartbooth 102 in the event of a power outage, or if their ability to operate the lock from the interior is impaired. A backup battery may also provide further redundancy in the event of power outage.

In some embodiments, a special purpose lock for the purposes of locking luggage will be included with the Smartbooth 102, enabling securing luggage in a variety of internal and external placements, contingent upon luggage quantity and customer preference. The locks may include, but are not limited to, cables, chains, or other material known in the art that can be locked or unlocked from inside the Smartbooth 102. In one embodiment, the lock may also utilize accelerometers to ensure that if there is tampering or movement of the luggage the person inside the Smartbooth 102 is alerted through internal visual and/or audio message in the Smartbooth 102 and through the consumer app through push notification or in app messaging.

The Smartbooth 102 may also have a dedicated WiFi router (not shown in FIGS. 1-6) to provide internet connectivity to users of the Smartbooth 102 or others nearby. The router may be provided free or for a fee. In certain embodiments, the WiFi router can also be used to count inbound attempted connections of mobile devices and/or computers as a proxy method to count people, determine proximity of people nearby, determine location, or to monitor bandwidth usage.

In some embodiments, the Smartbooth 102 will contain outlets (not shown) to charge personal electronic devices on the exterior of the Smartbooth 102, including, but not limited to, phones, tablets, computers, or other devices that need electricity to operate. In one preferred embodiment, charging stations will support wired or wireless charging, have voltage conversion adaptors, and adaptors for different plug configurations which vary by country. In some embodiments, devices will be able to be locked in a safe-style compartment that can be opened with a code. Payment can be made through the Smartbooth operating system app installed on a user's device or installed in, for example, the tablet of the Smartbooth via the payment system.

In certain embodiments, the Smartbooth contains tools enabling video conferencing, communication with operational staff, or others. On the interior of the Smartbooth, customers have the ability to mount a personal or work phone, tablet or other portable digital device. In some embodiments, once mounted on the portable device mount, that device's native camera, microphone, apps, and credentials can be used for video conferencing purposes. Additionally, in some embodiments, the interior of the Smartbooth 102 will have pre-installed and positioned cameras, screens, keyboard, and mouse controls for optimized video conferencing calls, leveraging third party or proprietary audio and video conferencing services. In some preferred embodiments, the interior of the Smartbooth is preferably equipped with a flip up desk 122, as shown in FIG. 2, and a phone and accessory shelf. In some embodiments, virtual reality hardware will be pre-installed and configured for the use of virtual reality conferencing, or for entertainment purposes. Virtual reality hardware may include but is not limited to headsets, visors, gloves, hand controllers, a computing system to run the Virtual reality software, and/or haptic suits to convey a sense of touch through application of pressure throughout various parts of the suit.

In certain embodiments, the Smartbooth 102 is equipped with sanitation devices for disinfecting surfaces within the Smartbooth 102 or otherwise periodically cleaning the interior of the Smartbooth 102. For example, the Smartbooth 102 may be equipped with disinfecting solution and/or cleaning wipes for use by the user. In other embodiments, the Smartbooth 102 has storage for cleaning supplies for access by an administrator or custodial staff at the location of the Smartbooth 102. The Smartbooth 102 may also have a dedicated channel to route liquid when spilled on the desk or on the floor. The liquid is routed to the exterior of the Smartbooth 102 or into a bladder that can be emptied or replaced. The Smartbooth 102 also has liquid sensors on the desk, in the water channels, and in the floor. When liquid comes into contact with the sensor, a message is sent to a service provider to maintain the Smartbooth.

It is another aspect of some embodiments of the present invention to provide a Smartbooth that automatically disinfects itself at predetermined times, such as after use or daily/nightly. For example, the Smartbooth may include devices that selectively expose its internal volume to an aerosolized mist of disinfectant solution. The disinfectant solution may be stored within a refillable or replaceable reservoir. Alternatively, a puck that releases disinfecting material for a predetermined amount of time is placed within the booth. A vent or venting system may be provided to facilitate removal of the disinfectant solution or material after a predetermined time. The contemplated disinfecting mist may be provided by at least one sprayer or nozzle interconnected to at least one of the inner surfaces of the Smartbooth walls, ceiling, or floor. In one embodiment, the nozzles are interconnected to a reservoir of disinfecting material and the mist is selectively controlled by a control system configured to direct disinfecting material from the reservoir to the at least one nozzle by controlling a valve and/or atomizer, for example.

One of skill in the art will appreciate that the booth may be purged with inert gas or gas harmful to pathogens (carbon dioxide, for example) to create the contemplated disinfecting environment. In this embodiment, the Smartbooth's door may be unlocked, vacancy verified, and/or lights, notifications, and/or alarms are used to indicate the booth has been exposed to potentially-dangerous materials. After the booth is vented or after the purge material has dispersed, an "all clear" notification can be used. One of ordinary skill in the art will appreciate that this enhanced disinfecting process may be performed only after a serious contamination event or off-hours.

Other embodiments of the Smartbooth includes devices that expose the booth interior to ultra-violet (UV) or microwave radiation for a predetermined amount of time. The UV radiation may be naturally occurring, wherein the Smartbooth includes one or more translucent or mesh panels that allow sunlight to enter into the booth. The contemplated UV-based system of one embodiment comprises at least one UV emitter interconnected to at least one of the Smartbooth walls, ceiling, or floor. A controller is provided that is configured to selectively power the at least one UV emitter.

In operation of one embodiment, the Smartbooth is locked automatically after use and cleaning personal are notified that booth cleaning is needed. In other embodiments, however, the booth is locked for automatic cleaning and/or disinfecting. Disinfecting of the booth's interior is performed for a predetermined amount of time automatically controlled or controlled remotely by regular maintenance personnel or by a third party. The contemplated automatic cleaning/disinfecting cycle can occur before access by a cleaning crew, after the cleaning crew performs their tasks, or can be standalone. The automatic cleaning/disinfecting cycle may employ a timer-based control system according to preset guidelines. In some embodiments, the booth doors or other openings are locked during the disinfection process.

Some embodiments also include the functionality wherein the Smartbooth is tested after disinfection to verify that it is free from pathogens or pathogens have been reduced below a recommended level. Further disinfection or a different disinfection method or protocol can be implemented if needed. In other embodiments of the present invention, sensors are provided that effectively "sniff" and analyze the air within the Smartbooth to ascertain the presence of harmful pathogens/toxins. If the amount of a harmful substance is greater than the predetermined threshold, the booth can be taken off-line for cleaning/disinfecting. Alerts and notifications as contemplated herein, may also be used to signal that the booth is or may be contaminated. Further, if an individual(s) is working within the Smartbooth, the test data can be used to potentially identify an infected individual. Accordingly, the contemplated booth may be used as a vestibule or checkpoint to "clear" individuals so they can proceed to their destination or quickly identify those who may be infected with a pathogen or toxin. One of ordinary skill in the art will appreciate that such booths may include additional data gathering devices, such as breathalyzers, body temperature sensors, infrared cameras, etc., that the occupant passively or directly interacts with.

In some embodiments, the Smartbooth 102 is outfitted with gaming hardware and can be used as a self-contained gaming and entertainment center. For example, certain embodiments provide users with gaming systems, controls, software, connectivity, and an enclosed environment to play games or to watch videos, television, or provide access to a browser in order to access the internet. In some embodiments, time in the Smartbooth 102 and/or game or entertainment time is charged to the user by the minute or in blocks of time. In some embodiments, games are played using browser-based games (running in a web browser as a client), PC-games (thick client, installed software onto a MacOS, Windows, or Linux operating system powered machine), app-based games running on mobile devices or tablets installed in the Smartbooth, or Virtual Reality games using VR game hardware.

In other embodiments, the Smartbooth 102 is outfitted with lighting, sounds, music, and video that provide a place for relaxation, meditation, or otherwise allows for a relaxation space. The Smartbooth 102 may also be outfitted with floor mats, hammock chairs, pillows, soft seating, or otherwise ergonomically comfortable spaces. Curated playlists and combinations of light hues and effects may also be customized by the user in these embodiments through an interface provided through the consumer mobile app, or through a user interface provided inside and/or outside of the Smartbooth 102 or connected to the booth operating system.

In some embodiments, the Smartbooth 102 may be designed primarily for sleep. For example, in certain embodiments, the Smartbooth 102 extends the functionality and attributes of the relaxation/meditation Smartbooth 102, as described above, to also include an area for users to lay prone and sleep. In these embodiments, time is charged to the user for the sleeping period, by the minute, or for blocks of time. In these embodiments, additional storage lockers for luggage may be included to facilitate overnight or extended periods of use of the Smartbooth 102.

In many embodiments, the screens and speakers 116 in the Smartbooth 102 can be leveraged for public service announcements or emergency messaging to warn occupants of the Smartbooth 102 or individuals outside of the both of fire, flood, severe weather, terrorist threats, active shooters, biological or chemical threats, and/or other dangerous situations. Where multiple Smartbooth 102 are installed in a single large location (e.g. airports, stadiums, and convention centers), and their specific locations are mapped by site administrators, hyper-local messages may be delivered by the public service/emergency messaging administrator and delivered to each user in each Smartbooth 102. In addition, the Smartbooth may comprise visual and audible alerts to let a user of the Smartbooth 102 know that an alarm (i.e., fire alarm) has been triggered. Redundancy in power supply/backup battery, as well as redundancy via multiple notification methods, may be part of increasing the certainty that the user receives, sees or hears any critical message or alarm.

In some embodiments, the Smartbooths 102 may be located in an outdoor area, either protected or unprotected from weather and/or the natural environment. These outdoor versions of the Smartbooth 102 are weatherproof, and, in certain embodiments, may also have solar panels, small scale wind turbines and local electricity storage with batteries. In these embodiments, the Smartbooths 102 may also be self-powered, and may also feed power back into the grid. In certain embodiments, charging stations for electric vehicles are available on the outside of the booth for charging of electric vehicles either driven by people or autonomously, including cars, trucks, and/or aerial or terrestrial drones or robots.

In certain embodiments, sound may be emitted through embedded speakers 116 inside the Smartbooth and on the exterior. For example, sound may be transmitted through speakers 116 in the Smartbooth 102 to convey messages, enable direct communication with Smartbooth occupants with Smartbooth administrators or support personnel, or to provide entertainment services, such as music or sound for movies or video games. In some embodiments, a 'hiss' or other sounds may also be played through speakers 116 to mask other unwanted sounds from outside the Smartbooth 102. This sound masking technique, also known as white noise or brown noise, is an additional method to keep others from hearing sound from inside the Smartbooth 102, or for a Smartbooth occupant to hear sound from outside the Smartbooth 102.

Figure 6:
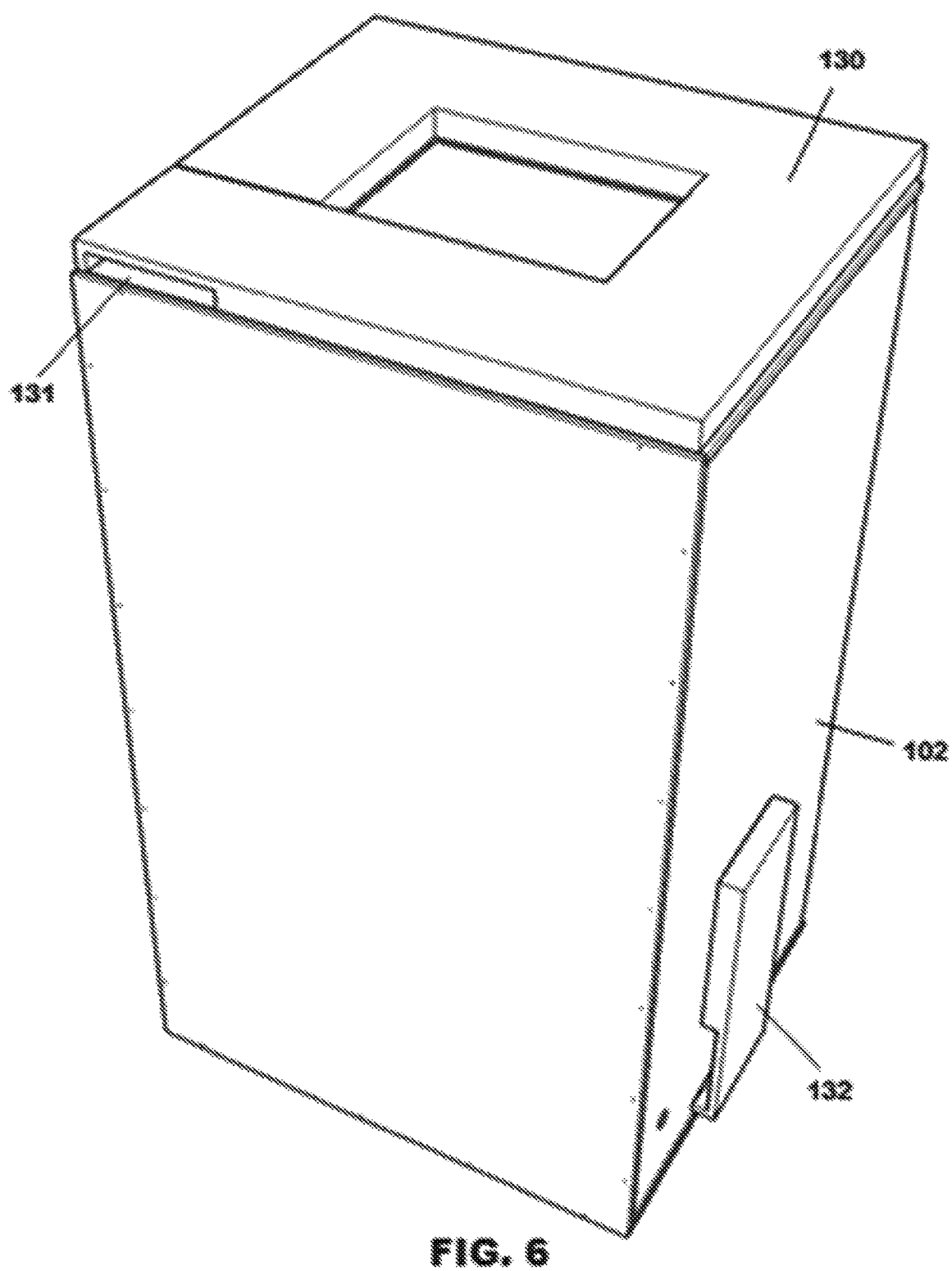
FIG. 6 is a rear perspective view of the system according to the embodiment of FIG. 5.
Figure 7:
FIG. 7 is a detailed elevation view of the system shown in FIG. 5.
Figure 8:
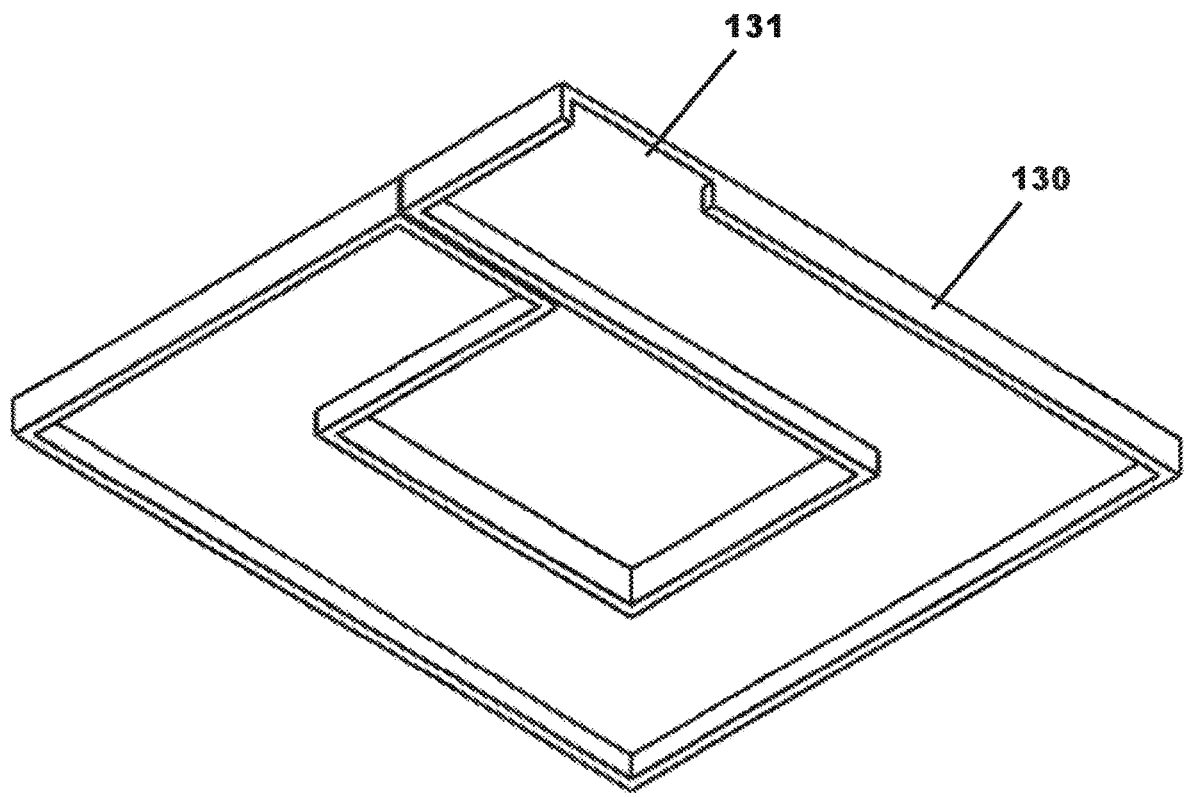
FIG. 8 is a detailed perspective view of the system shown in FIG. 5.
Figure 9:
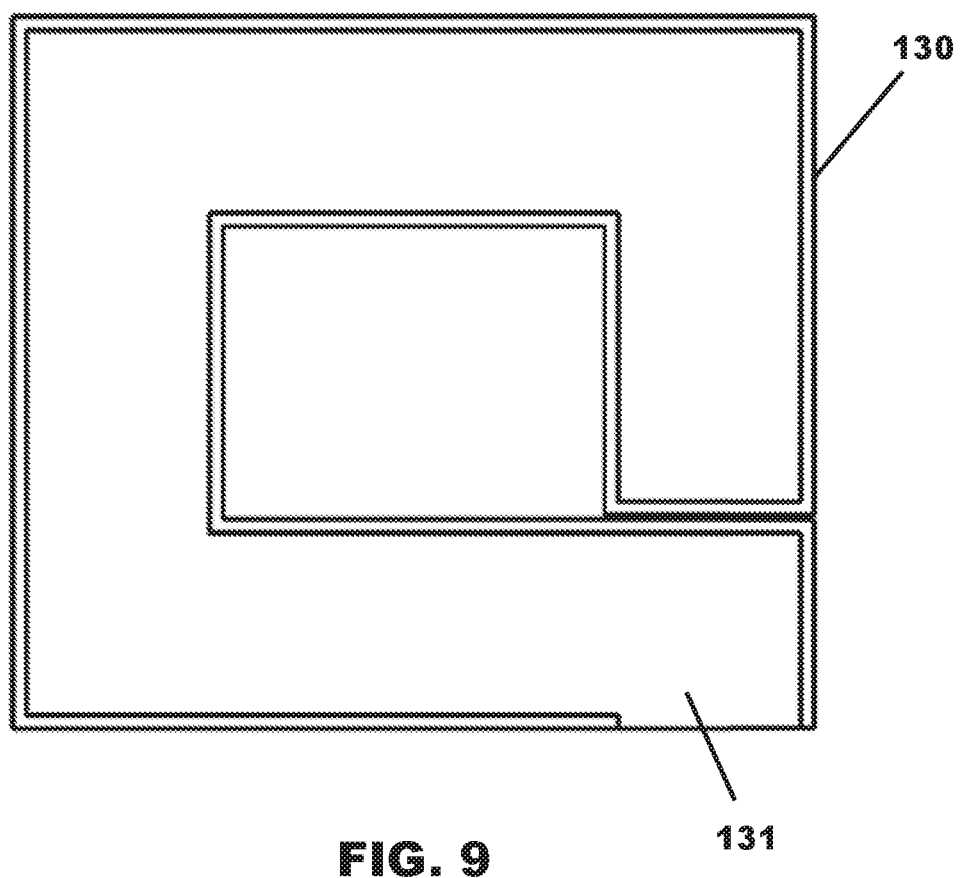
FIG. 9 is a detailed plan view of the system shown in FIG. 5.
Figure 10A:
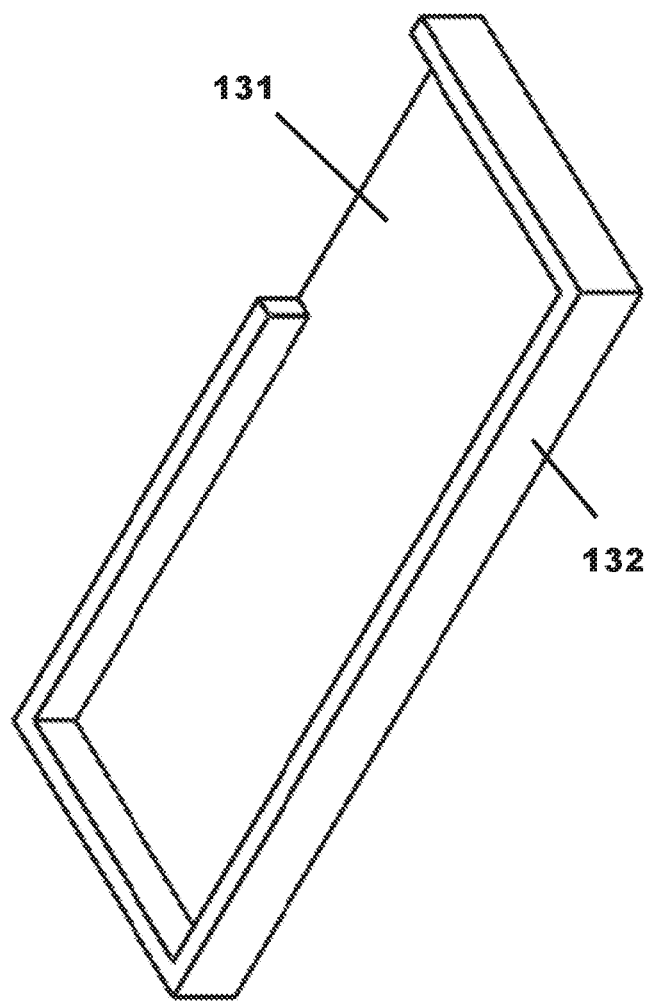
FIG. 10A is a detailed perspective view of the system according to another embodiment.
Figure 10B:
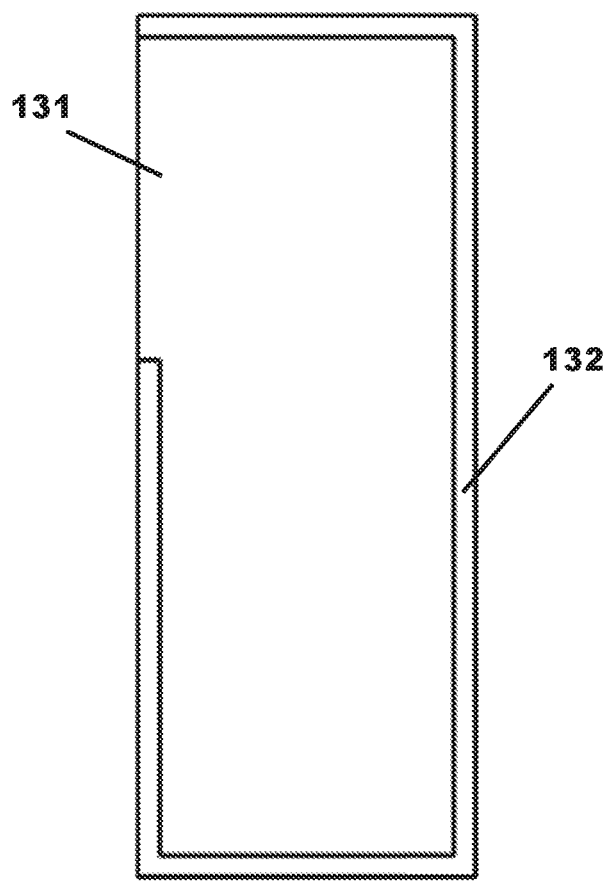
FIG. 10B is a detailed plan view of the system shown in FIG. 10A.

Referring to FIGS. 7-10B, the Smartbooth 102 may comprise one or more baffles or equivalently arranged structures to ensure proper ventilation while achieving the privacy and sound requirements of the user. As shown in FIG. 7, the baffles may be located within the ceiling or roof structure of a Smartbooth 102. The baffles are preferably arranged in a "labyrinth" arrangement, as shown in FIG. 8, and are also preferably made of an acoustically absorbent material. In this manner, baffles or equivalent portions of the enclosure may be arranged in a cascading manner as shown in FIGS. 8-9 in particular. This "labyrinth" arrangement of baffles ensures that no ambient noise interferes with the user's enjoyment and use of the Smartbooth 102. Furthermore, the arrangement shown in FIG. 6 provides adequate ventilation to the user or users while secured within the Smartbooth 102.

Figure 5:
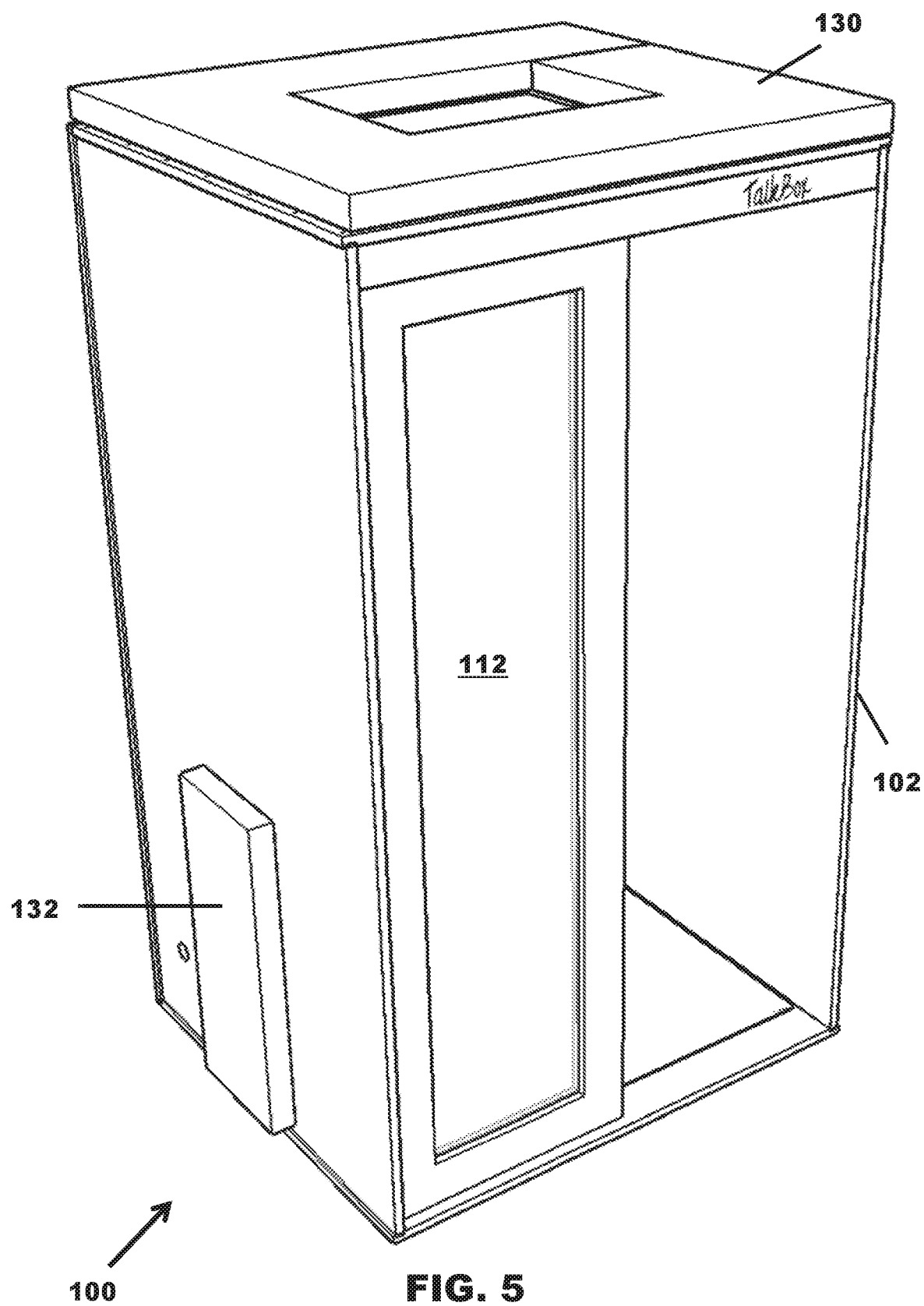
FIG. 5 is a top perspective view of the system according to another embodiment.

Alternatively, the Labyrinth of baffles 130 may be arranged above the ceiling or roof structure of the Smartbooth 102, as best shown in FIGS. 5-6. The Smartbooth 102 may also be equipped with a secondary baffle 132 as shown in FIG. 5. In either instance, the baffles 130 may include an opening 131 to permit air and ventilation through the baffles 103, 132 while at the same time preventing unwanted noise to infiltrate the Smartbooth 102, or for private conversations to be heard outside the Smartbooth. Additional views of the baffles 130 are shown in FIGS. 8-9 and of baffles 132 in FIGS. 10A-10B. It is expressly understood that baffles 130, 132 may be positioned in different locations than shown in FIGS. 7-10B.

Figure 11A:
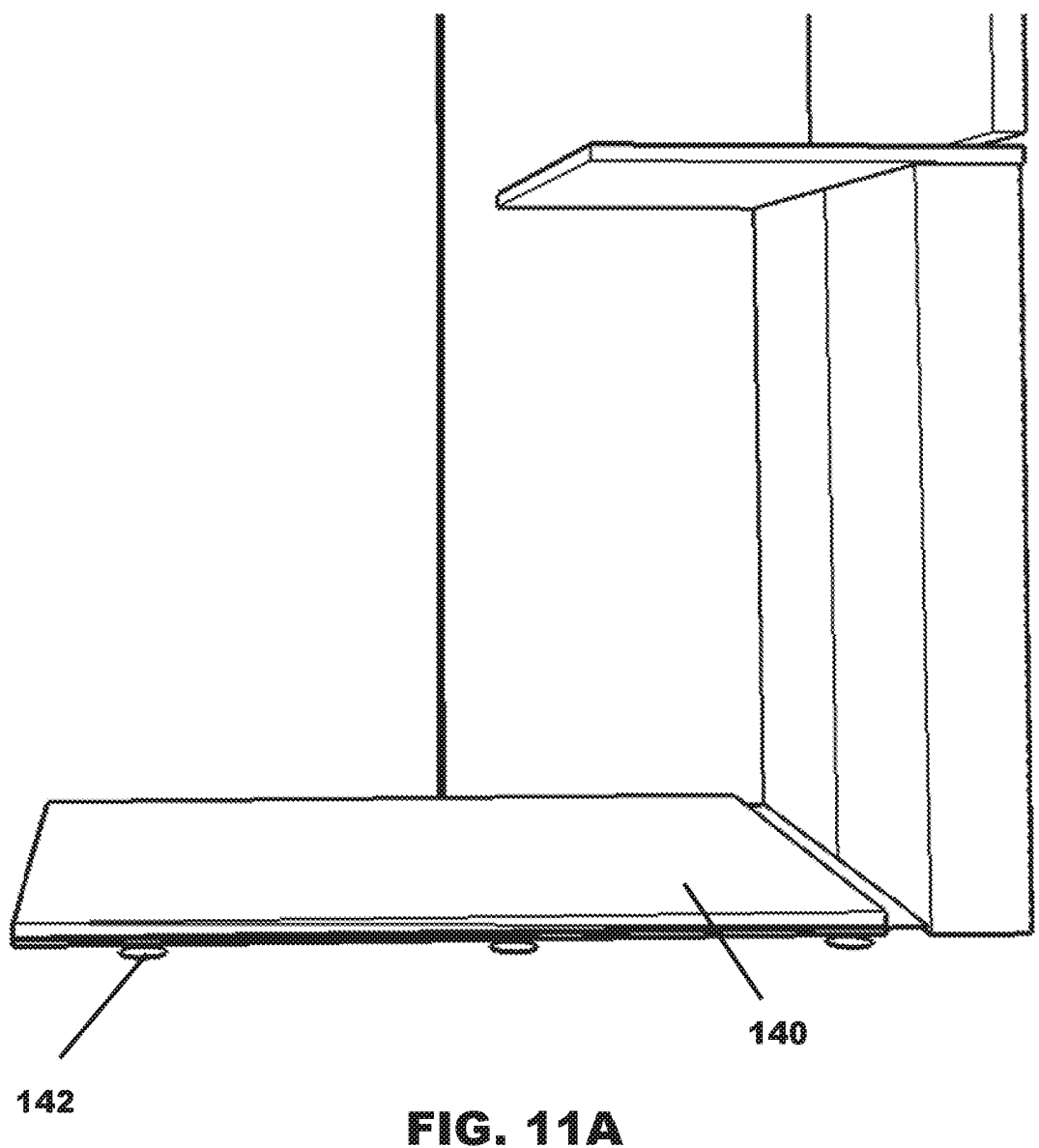
FIG. 11A is a partial elevation view of the system according to another embodiment.
Figure 11B:
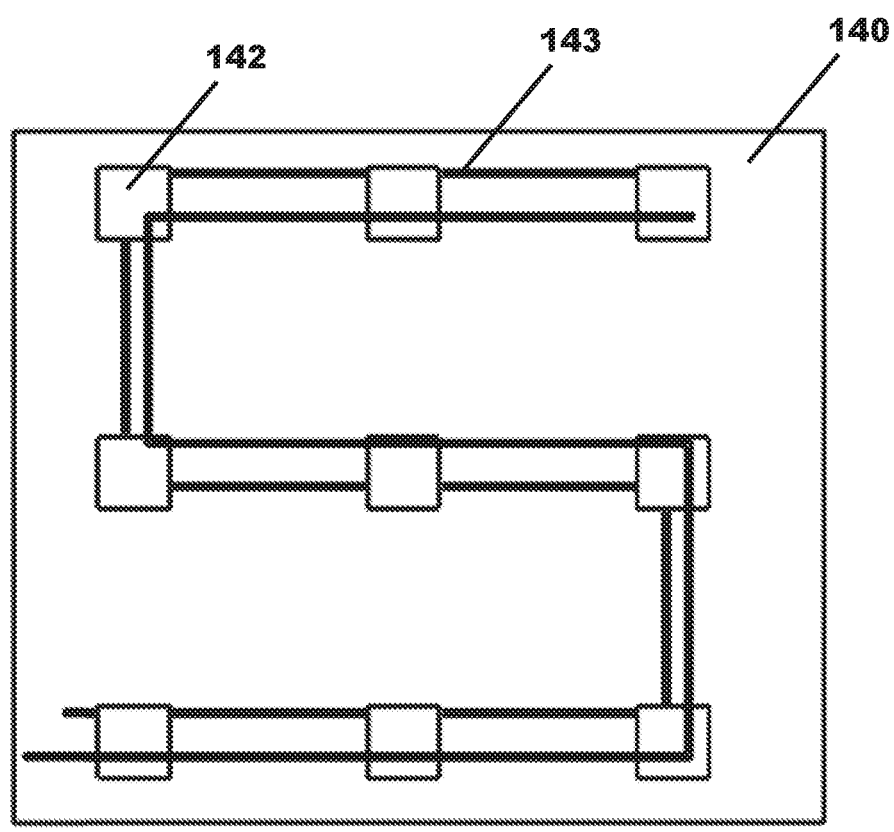
FIG. 11B is a detailed plan view of the system shown in FIG. 11A.
Figure 11C:
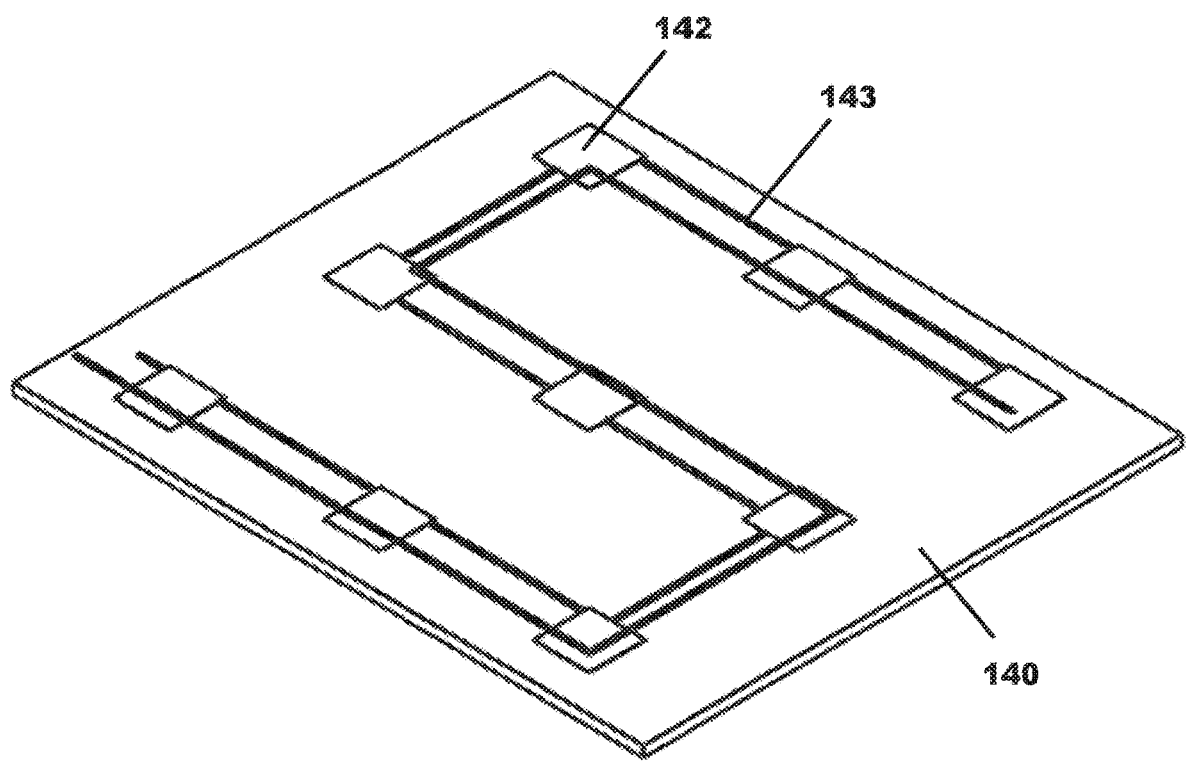
FIG. 11C is a perspective view of the system shown in FIG. 11A.
Figure 11D:
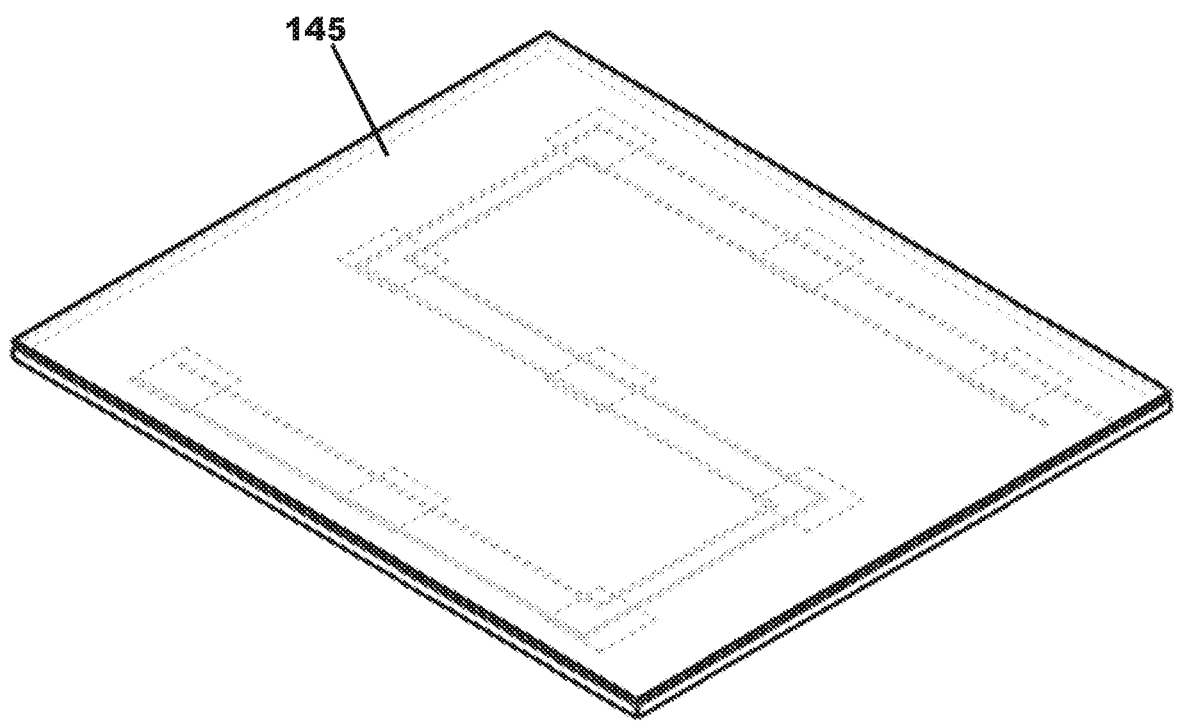
FIG. 11D is another perspective view of the system shown in FIG. 11A.

Additional aspects of the present disclosure are shown in relation to FIGS. 11A-12C appended hereto. In these embodiments, the floor of the Smartbooth 102 is shown in detail to illustrate the use of sensors according to two embodiments of the present disclosure. In FIG. 11A, the Smartbooth 102 is shown in a partial elevation view to better illustrate the location of sensors beneath the floor surface 140 of the Smartbooth 102. Referring to FIGS. 11B-D, the floor 140 may comprise a series of pressure sensors 142 interconnected by wiring 143 that permits signals received by the sensors 142 to be routed to the computational machinery described above. Each sensor 142 may be independent or may be redundant. The sensors 142 may be configured to detect even a slight pressure applied to the floor 140. As shown in FIG. 11D, the sensors 142 may also comprise a conductive fabric or cover 145 to protect the sensors 142 and/or distribute the sensing or pressure across the cover 145 to individual sensors 142. In this manner, a pressure within the Smartbooth 102 as slight as a spilled liquid or other debris may be sensed. In other embodiments, the sensors 142 are configured to sense a greater pressure.

Figure 12A:
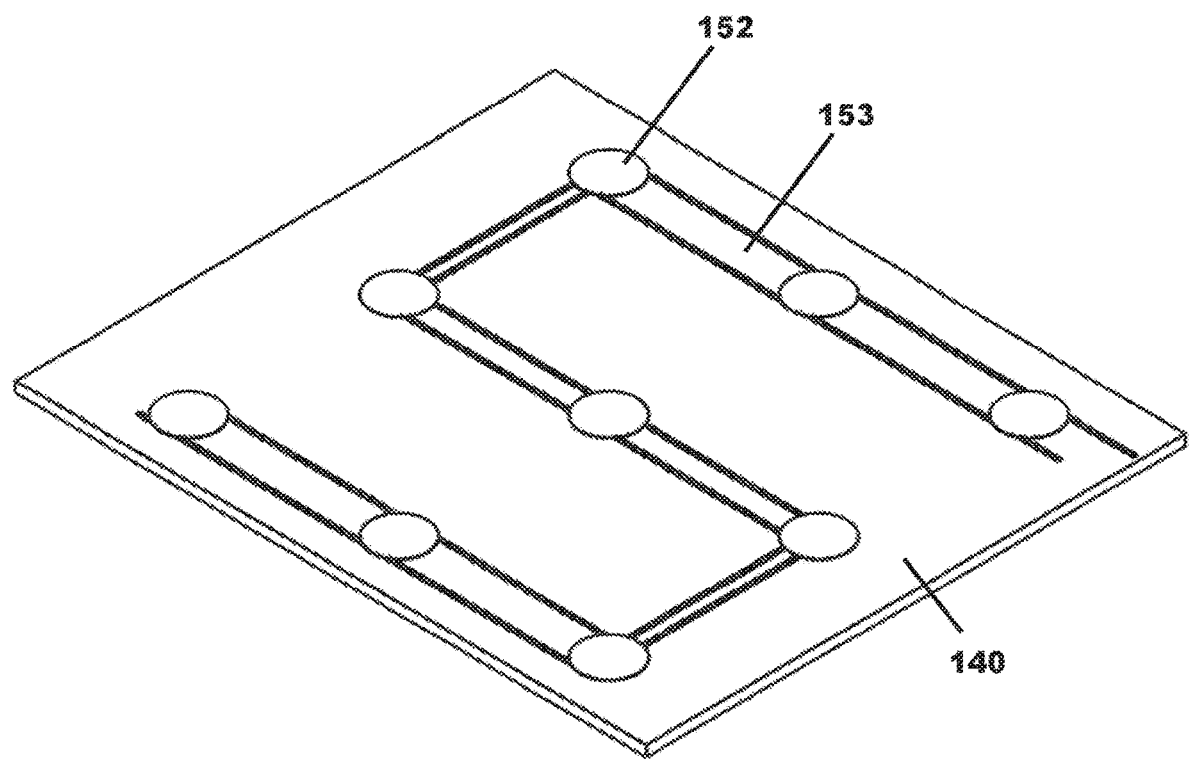
FIG. 12A is a perspective view of the system according to another embodiment.
Figure 12B:
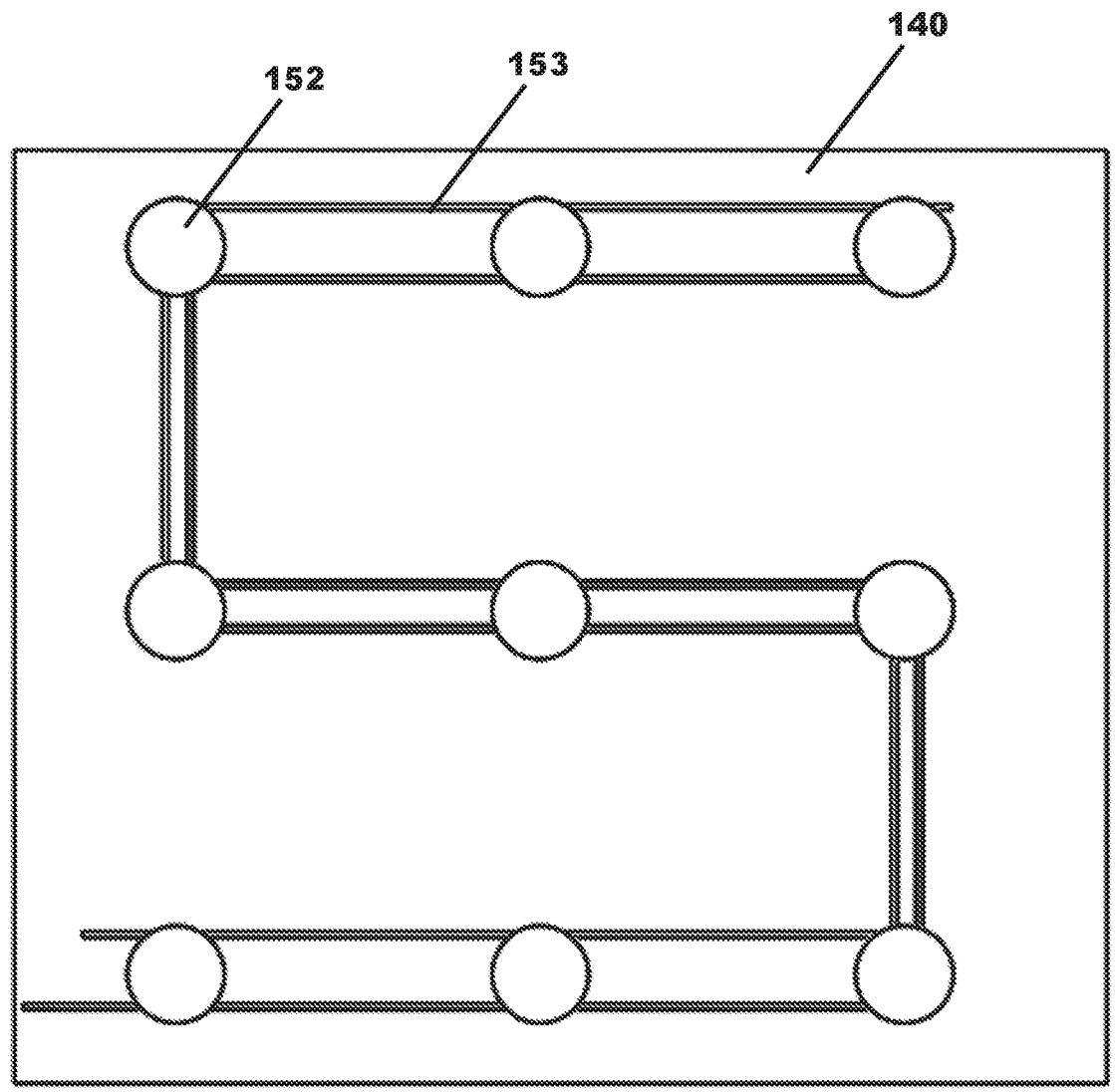
FIG. 12B is a detailed plan view of the system shown in FIG. 12A.
Figure 12C:
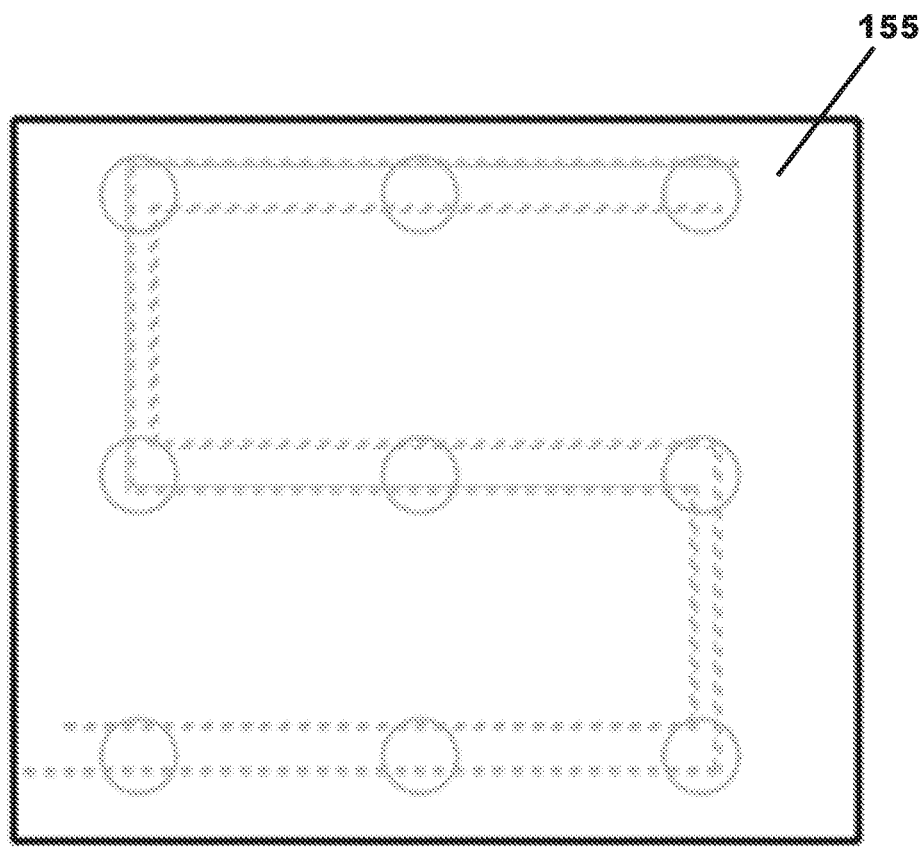
FIG. 12C is another detailed plan view of the system shown in FIG. 12A.

A similar embodiment is illustrated in connection with FIGS. 12A-12C, wherein the floor 140 comprises a series of force sensors 152. The force sensors 152 may be comprised of a pressure sensitive material, such as Velostat (or equivalent), and capable of measuring the electronical resistance across the floor 140 of the Smartbooth 102. The change in resistance permits detection of a person within the Smartbooth 102, or the absence of a person. The sensors 152 may be in electrical communication 153 with the computational machinery described herein, and may further be relayed to an administrator or to a local maintenance or other authority. Variations on the number and location of sensors 152 and configuration of wires 153 is contemplated for the purpose of this invention. As shown in FIG. 12C, a cover 155 may also be provided with the force sensors 152 described in this embodiment.

System Applications, Modules & Software

According to embodiments, the system comprises software application/modules that will now be described in detail. Applications/modules are preferably configured to run on a computer server or similar computational machinery. In one embodiment, the system and associated modules preferably comprise one or more user interfaces and displays. The system and modules may be stored or operated on a computing environment, wherein the devices, servers, modules, etc. may execute. The computing environment preferably includes one or more user computers. The computers may be general purpose personal computers (including, merely by way of example, personal computers, and/or laptop computers running various versions of Microsoft Corp.'s Windows and/or Apple Corp.'s Macintosh or iOS and/or Linux and/or Google's Android or Chrome operating systems) and/or workstation computers running any of a variety of commercially-available UNIX or UNIX-like operating systems.

Computational machinery (e.g., computers) described herein may also have any of a variety of applications, including for example, database client and/or server applications, and web browser applications. Alternatively, the user computers may be any other electronic device, such as a thin-client computer, Internet of Things devices (such as a Raspberry Pi or particle photon), Internet-enabled mobile devices such as an iPhone or Android device, a mobile tablet computer such as an iPad or Android powered touchpad, and/or personal digital assistant, capable of communicating via a network and/or displaying and navigating web pages or other types of electronic documents. Any number of user computers may be supported.

The computing environment described according to this embodiment preferably includes at least one network. The network can be any type of network familiar to those skilled in the art that can support data communications using any of a variety of commercially-available protocols, including without limitation SIP, TCP/IP, SNA, IPX, AppleTalk, and the like. Merely by way of example, the network maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, the Bluetooth protocol known in the art, and/or any other wireless protocol); and/or any combination of these and/or other networks.

The system in varying embodiments may also include one or more server computers. One server may be a web server, which may be used to process requests for web pages or other electronic documents from user computers. The web server can be running an operating system including any of those discussed above, as well as any commercially-available server operating systems. The web server can also run a variety of server applications, including SIP servers, HTTP servers, FTP servers, CGI servers, database servers, Java servers, and the like. In some instances, the web server may publish available operations as one or more web services.

According to certain embodiments, the computing environment may also include one or more file and or/application servers, which can, in addition to an operating system, include one or more applications accessible by a client running on one or more of the user computers. The server(s) may be one or more general purpose computers capable of executing programs or scripts in response to the user computers. As one example, the server may execute one or more web applications. The web application may be implemented as one or more scripts or programs written in any programming language, such as Java™, C, C#, or C++, and/or any scripting language, such as Perl, Python, or TCL, as well as combinations of any programming/scripting languages. The application server(s) may also include database servers, including without limitation those commercially available from Oracle, Microsoft, Sybase™ IBM™ and the like, which can process requests from database clients running on a user computer.

In embodiments, the web pages created by the application server may be forwarded to a user computer via a web server. Similarly, the web server may be able to receive web page requests, web services invocations, and/or input data from a user computer and can forward the web page requests and/or input data to the web application server. In further embodiments, the server may function as a file server. Although the foregoing generally describes a separate web server and file/application server, those skilled in the art will recognize that the functions described with respect to servers may be performed by a single server and/or a plurality of specialized servers, depending on implementation-specific needs and parameters. The computer systems, file server and/or application server may function as an active host and/or a standby host.

In embodiments, the computing environment may also include a database. The database may reside in a variety of locations. By way of example, database may reside on a storage medium local to (and/or resident in) one or more of the computers. Alternatively, it may be remote from any or all of the computers, and in communication (e.g., via the network) with one or more of these. In a particular embodiment, the database may reside in a storage-area network ("SAN") familiar to those skilled in the art. Similarly, any necessary files for performing the functions attributed to the computers may be stored locally on the respective computer and/or remotely, as appropriate. In one set of embodiments, the database may be a relational database, which is adapted to store, update, and retrieve data in response to SQL-formatted commands.

The computer system may also comprise software elements, including but not limited to application code, within a working memory, including an operating system and/or other code. It should be appreciated that alternate embodiments of a computer system may have numerous variations from that described above. For example, customized hardware might also be used and/or particular elements might be implemented in hardware, software (including portable software, such as applets), or both. Further, connection to other computing devices such as network input/output devices may be employed. The Smartbooth operating system will collect data and analytics for individual Smartbooths and transmitted to a remotely hosted database server to capture data from all Smartbooths connected into the system. Data captured by sensors may include but are not be limited to: 1) temperature, humidity, barometric pressure, inside and outside of the Smartbooth; 2) sensors configured to detect proximity, including whether the Smartbooth is occupied by a person or persons, including the time duration of the occupancy; 3) sensors configured to determine whether a person or persons occupying the Smartbooth is/are safe; 4) sensors configured to detect the state of cleanliness of the Smartbooth, including by comparing of before and after pictures prior to a new occupant arrives vs after the occupant leaves the session in the Smartbooth; 5) sensors configured to determine whether the occupant or occupants of the Smartbooth has paid for the use of the space; 6) sensors utilized to enhance the quality and content of advertisements served, number of advertisements viewed, number of impressions delivered, how many people saw an advertisement, etc.; 7) sensors configured to detect whether there are other objects that are not people within the Smartbooth; 8) sensors detecting an open/closed state of the door; 9) sensors configured to monitor decibel levels inside and outside of the Smartbooth; 10) sensors configured to detect the amount of weight contained within the Smartbooth; 11) sensors configured to monitor light levels within the Smartbooth; 12) sensors that detect the presence of liquid on the desk or floor of the Smartbooth; 13) sensors configured to monitor power consumption of electrical components of the Smartbooth; 14) sensors connected to feeds of video collected from cameras mounted on the interior or exterior of the Smartbooth and/or not mounted to the Smartbooth but capture the exterior of the Smartbooth in the video feed; 15) sensors connected to feeds of audio collected through microphones inside and outside the vicinity of the Smartbooth; 16) sensors configured to capture the amount of data transmitted into and out of the Smartbooth; 17) sensors to detect pathogens and/or the degree of Smartbooth disinfection; and, 18) sensors configured to determine which applications, content, services or features of the Smartbooth are used and for what frequency or duration. These sensors and the data collected allows product and services optimization of the Smartbooth, including for purposes of adjusting locations and identifying patterns in data that allow for improvements in usage, revenue, cleaning, disinfection need, security, etc.

According to one embodiment, the server may include one or more components that may represent separate computer systems or electrical components or may software executed on a computer system. These components include a load balancer, one or more web servers, a database server, and/or a database. The load balancer is operable to receive a communication from the mobile device and can determine to which web server to send the communication. Thus, the load balancer can manage, based on the usage metrics of the web servers, which web server will receive incoming communications. Once a communication session is assigned to a web server, the load balancer may not receive further communications. However, the load balancer may be able to redistribute load amongst the web servers if one or more web servers become overloaded.

In embodiments, one or more web servers are operable to provide web services to the user devices. In embodiments, the web server receives data or requests for data and communicates with the database server to store or retrieve the data. As such, the web server functions as the intermediary to put the data in the database into a usable form for the user devices. There may be more or fewer web servers, as desired by the operator.

In this embodiment, a database server is any hardware and/or software operable to communicate with the database and to manage the data within the database. Database servers, for example, SQL server, are well known in the art and will not be explained further herein. The database can be any storage mechanism, whether hardware and/or software, for storing and retrieving data.

Various user interfaces and displays are also the subject of this disclosure. The user interface may comprise a display for viewing on a mobile device, such as a smart phone, tablet or laptop style computing device. The user interface in this embodiment preferably comprises an interactive dialog display, which may be in the form of a dialog box, window or equivalent. The user interface may be configured to automatically resize and reformat the interactive dialog display depending on the viewable area of the device on which the user interface is displayed. The user interface may also accommodate a variety of communication modalities, including both written and oral communication. Verbal communication may be in interpreted by a smart speaker that leverages speech recognition through the natural language processing (NLP) engine described below, or through other technologies that utilize speech to text and/or speech recognition technologies. Speech that is recognized by the system may, in one embodiment, be displayed back to the user visually on a screen or other display within the Smartbooth 102.

The user interface may take many forms. For example, the user interface may include multiple panes for displaying information to the user simultaneously, or it may allow for screen mirroring, such that the user interface on the phone becomes displayed and usable on a monitor then controlled by phone, keyboard or touchscreen. The user interface may be comprised of a keypad and screen for both input by a user and display of information to the user. The user interface may accept auditory commands by a user speaking into a microphone embedded in a 'smart speaker' that will use speech recognition techniques and/or the NLP engine to interpret speech and respond with events via sound, physical events, or message on screen. The user interface may occur through a separate application contained on a mobile device such as an iOS or Android mobile device. The user interface may include interfaces through a virtual environment accessed via a screen or Virtual Reality hardware. The user interface may be located such that it is external to the Smartbooth 102 enclosure or from within the Smartbooth 102. The user interface may comprise the detection of the presence of a mobile phone or device to uniquely identify a person entering the booth through an RFID reader, Bluetooth communication or other Near Field Communication technologies such as physical beacons that identify the presence of a uniquely identified device, or protocols for access control, and may comprise a biometric reader such as through a camera for facial or body recognition, a fingerprint scanner, eye scanner, DNA scanner, infrared camera, or other biometric reader device for ensuring only the authorized user(s) of the Smartbooth 102 are permitted access to the interior of the enclosure. The user interface may also be through touch-screen interaction through touching the screen for selection. The user interface may further comprise one or more indicia to alert the user of an incoming call or the presence of another anticipated user in proximity to the Smartbooth 102, such that the user may permit entry of the permitted additional user(s). The indicia may also indicate a boarding sequence, a selected service (described below) becoming available or completed, a successful transmission from the secure data hub located within the Smartbooth 102 or other desired event.

In one embodiment, in addition to the software applications 106 identified above, a consumer version of a TalkBox app (not shown) is available for download (including by way of example through Apple and Google Play), for use in identification of intended SmartBooth 102 to use in specificity (in the case where multiple Smartbooths are deployed in near proximity) payment, booking/scheduling, and selection of features available in the Smartbooth 102. In embodiments, the Smartbooth 102 and associate applications/modules: (1) allows a user to purchase blocks of time via the payment system 110 based on a proprietary algorithm; (2) collects and validates payments via the payment system 110; (3) books and reserves blocks of time to use the service via the payment system 110; (4) controls access to the Smartbooth 102 and its services via a locking mechanism 112; (5) serves and traffics media and advertisements to displays 114 and speakers 116; (6) automates hardware behaviors such as lighting 118, sounds 116, door lock 112, olfactory experience, and playing media; (7) consumes and transmits data 108 from environmental observation hardware (not shown) including video cameras, microphones, and sensors of various types such as light, pressure, laser, audio, and environmental sensors; (8) connects to the internet 108; (9) connects and interfaces with the Smartbooth Backend and consumer app through the internet 108 to relay data, audio and video; (10) manages integrations and entitlements with third party services integrated into the Smartbooth 102; and (11) tracks location through the use of GPS chips and location services native to mobile devices; (12) identifies the specific Smartbooth intended for use through the entry of an alphanumeric code, or through the capturing of an image of a QR code through the camera within the consumer app, or through the native camera app on the mobile device. (13) determines the amount of time spent in the booth by the occupant and will over time, award loyalty points for the occupant, awarded in the account of the occupant. (14) provides a map of the locations of other Smartbooths in proximity and across the globe (15) provides the ability to store and configure account settings, personal preferences, and security measures such as passwords (16) credentials for integrated 3rd party applications (such as Google accounts), services (such as VPN, remote desktop, or encryption services); content providers (such as Netflix or other content streaming services, gaming services such as Epic games) Functionality within the consumer phone application, that is relevant to the experience and display within the Smartbooth, will be duplicated natively or through APIs so that they are accessible and available for the occupant of the Smartbooth from the interfaces included in the Smartbooth. In some embodiments, users may book time ahead of time through a Talkbox website, the application/module, or another service, in which case the door will remain locked for a predetermined amount of time prior to the booked session. A PIN code of (alphanumeric digits) or other form of credential may be issued to the user, which can be used to unlock the door, which would otherwise remain in a locked state. The code will be valid for the time block that has been booked ahead of time so that the user may leave the booth, which can auto-lock upon exit, and return at a later time by re-entering or otherwise supplying the code to the Smartbooth 102.

The TalkBox Backend, as mentioned above, is a hosted server-side application and database managed in a separate physical location from the Smartbooth 102 that captures and stores sensor data and logs access and usage of the Smartbooth 102. Sensor data may be obtained via measurements from weight/pressure sensors, door open/close sensors, lock operation, light/fan operation, power consumption, fluid sensors, audio visual usage, advertising, and environmental sensors. This leads to optimization of the overall fleet of deployed Smartbooths, for the purposes of intelligence for product improvement, ad serving, cleaning, security, targeted messaging, location and personalization services.

In embodiments, the TalkBox Backend also provides administrative tools to manage advertisements 114; media and messaging for display through audio speakers 116; operational and maintenance controls and status for each individual Smartbooth 102; remote administrator operation of Smartbooth features and functions; and communication with Smartbooth occupants, service providers, or other interested parties.

In embodiments, the Smartbooth 102, which contains the requisite hardware and software features and functionalities, is packaged and licensed for integration into any third-party booths. In this embodiment, the TalkBox Backend will be provided as a managed service.

In one preferred embodiment, the Smartbooth 102 provides environmental state detection with automated and conditional responses. The Smartbooth 102 combines a variety of internal and external sensor technologies, wherein based on a single or combination of multiple input(s)/state(s), a conditional response is subsequently and automatically triggered. In these embodiments, the presence of a user may be detected and monitored. When, for example, the Smartbooth is occupied, indicators may be provided showing that the booth is occupied, such as, but not limited to, visual indicators on the booth, an alert to a mobile device, a status indicator in an app, internet, intranet, or website, or other digital channel that is data driven. This embodiment then enables the purposes of collection of payment; tracking and recording usage of the booth, booth features and functions; and then enabling payment collection, account tracking, and other forms of commercial engagement whereby the occupant of the Smartbooth is subject to terms and conditions by entering the Smartbooth and or using the features and functionality provided by the Smartbooth.

For example, pertaining to internal sensors, in one preferred embodiment the Smartbooth 102 detects the presence of customers and their corresponding payment status via gravitational pressure, ultrasonic, light (photoresistors, photodiodes, and phototransistors), infrared, laser, video analytics, facial recognition technology/software, mobile phone signal detection, capacitive, proximity and/or motion sensors. Smartbooth 102 compares the detected presence of an individual, combined with the current system time, against a uniquely-generated session identification number and its expiration timestamp to determine a paid or unpaid presence.

In one embodiment, the video analytics engine will be comparing the picture of a clean Smartbooth against the snapshot of the Smartbooth after each use to communicate the cleanliness of each Smartbooth. Upon detection of a Smartbooth needing cleaning, an alert will go to an administrator to inspect further any cleaning needed, and to schedule cleaning service as needed. In another embodiment, the facial recognition functionality can recognize and welcome new or regular users. Further, to discourage criminal behavior within the Smartbooths, or usage of the Smartbooths by identified criminals, facial recognition technology will be used to report to the appropriate authorities any identified criminals.

As alluded to above, the Smartbooth 102 uses a variety of methodologies to incentivize payment for use of the Smartbooth 102, and disincentivize use without payment. For example, in one embodiment, if an occupant is inside the Smartbooth and has not paid, internal speakers will broadcast noise so that it is louder inside the Smartbooth than outside of the Smartbooth. The Smartbooth will also blink or modify internal lights in a pace or manner that may incentive payment. In some embodiments, screens 120 inside the Smartbooth will show messaging to indicate that payment is necessary with instructions about how to make payment. Other embodiments may also continue to charge the last person to exit the Smartbooth 102. If someone does not end their session actively and shut and lock the door behind them, they will continue to be charged until they proactively cancel the session. In another embodiment messaging, sounds or video may be broadcast outside of the Smartbooth 102 to indicate that payment has not been made by the occupant inside the Smartbooth.

System Services

In embodiments, the Smartbooth may also facilitate the delivery of services to the user, including services that are in close proximity to the particular Smartbooth reserved (or in use) by the user. Examples of such services include delivery services (both to and from a workspace), printing/copying services, document certification services, secure data transmission, currency exchange, translation services and other services. In certain cases, the location of a user in a secure workspace would facilitate the provision of these services from service providers located in the vicinity of the workspace and arranged by a user of the systems and methods described herein.

For example, the Smartbooth 102 may include a Federal Express or equivalent delivery service receptacle on the exterior of the Smartbooth 102 but accessible form the interior of the Smartbooth 102. In this manner, a user may compose and execute a document and immediately deposit the same for pickup for a schedule or unscheduled delivery service. Dining and other food delivery may be provided and arranged by the user in a similar manner. Variations on this embodiment with other services are contemplated.

In embodiments, services may include the ability to order food or beverages; or to order services, such as shoe shining services, messages, or haircuts, or other appointment related services that are transactional in nature. Another embodiment may be to leverage third party content services that require account access, such as news services in form of web content delivery, or through streaming content channels typically delivered via cable news networks, but not limited to content type, content channel, or content provider. Any content that can be delivered digitally may be an embodiment.

In addition, in some embodiments, when active TalkBox mobile application users are in the proximity of, but not using Smartbooth via paid sessions, a Smartbooth's external advertising 114 content may be dynamically refreshed to cater to a specific user's actual or likely preferences. The Smartbooth 102 may also monitor foot traffic on the exterior of the Smartbooth 102 using environmental sensors and detection of signals from mobile devices to count the number of viewers of its advertisements.

In some preferred embodiments, the Smartbooth 102 also has voice-controlled speakers connected to voice powered assistants such as Amazon's Alexa, Google Home, or Apple's Siri. Operational instructions, payment information and other services may also be provided using voice activated assistants, such as the examples listed above.

Throughout the operating hours of Smartbooth 102, remote operators may be standing by to assist with system and customer-initiated issues via video and/or teleconference (if equipped), and monitor and override Smartbooth settings if/as necessary.

In some embodiments, the Smartbooth 102 may externally display advertisements, both to draw attention to the Smartbooth 102 for potential use by a user, but also to display marketing and sales materials from third-party companies that choose to display their content through the various Smartbooth 102 interfaces. There are multiple channels through which the Smartbooth 102 will display advertising or messaging, as a publisher. The Smartbooth 102 will preferably have digital displays on the interior and exterior of the enclosure, in a number of configurations. Additionally, the Smartbooth 102 will preferably have speakers 116 on both the interior and exterior through which advertising or marketing messages may be broadcast.

In some embodiments, the digital displays 114 will serve and traffic advertisements by leveraging the Smartbooth 102, which will interface with Ad Servers, DMPs, Ad exchanges or other third party advertising technology providers and sources of ad buyers and advertisements which can then be displayed to consumers of the ads. Media for advertisements will be cached locally or served dynamically through interfaces with third parties.

Adaptive & Machine Learning

In embodiments, the system may further comprise one or more logic or decision trees described in greater detail herein. In varying embodiments, the system may be adaptive and able to learn new functions or acquire additional knowledge through the course of interactions with a user. In embodiments, multiple enclosures may be provided with distinct or partially overlapping capabilities, and in certain embodiments are configured to communicate and interact with one another to more efficiently process requests from the user(s) and provide information and/or services relevant to the user(s) request.

In embodiments, the system may comprise a natural language processing engine configured to determine the appropriate analysis, information and/or service(s) to supply to the user in response to an inquiry, instruction or command, including through the use of logic or decision trees described in greater detail below. In embodiments, the system may comprise a natural language processing module that can be selectively accessed or integrated with the system. In embodiments, the system may further comprise a module for foreign language processing and may further comprise a language identification module configured to determine a language to be associated with a particular user. The system may comprise additional modules, including but not limited to a communication analysis module, a speech to text module, and a voice analysis module. The system may be configured to receive the at least one input and translate each of the at least one inputs into a native language before processing the inquiry, instruction or command.

In embodiments, a decision tree may be configured for use by the system relating to the particular context of the inquiry or request of the user. In embodiments, several different contextual learning engines may be supplied simultaneously, each comprising a unique decision tree or in some instances several decision trees. Each decision tree may comprise a plurality of nodes, wherein each node may comprise a logical routine, a sub-routine, an input function, an output function, and equivalent processes. Each node may comprise multiple of the foregoing exemplary processes. Furthermore, context and meaning may be maintained during a dialog through the use of one or more nodes in a decision tree, which may further comprise the structure of a task to be performed jointly through dialog with a user. The system may comprise an execution model for conducting dialog with the user to maintain appropriate context and result in successful completion of the desired activity.

In embodiments, decision trees may interface with a module for supplementing the reasoning and inference rules inputted to the system. In other embodiments, the decision trees may comprise a context manager with access to one or more third-party databases for ensuring proper context. Variations on these combinations are considered within the scope of the present disclosure.

In embodiments, the system may be further configured to determine whether any additional information is required to complete a task or fulfill a specific decision tree. If a determination is so made, the system may be configured to generate prompts for each piece of missing information from a user. The prompts may be through the dialog with the NLP engine, through one or more of the user interfaces described above, or through a different modality.

A speech biometric engine may be supplied if data security is required for access to the system, or information and/or services requested by the user. In these instances, the system may select a decision tree associated with the user and extract the requested information from a secure data repository. If the user is not recognized, biometrically or otherwise, the system may terminate the user's session.

In embodiments, the system may comprise an adaptive learning capability wherein, if a relationship between the at least one input received by the system and the decision tree cannot be determined, a machine learning engine is further provided and configured to process the at least one input. By way of example but not limitation, embodiments disclosed herein further comprise the ability to generate one or more nodes associated with a decision tree. The system further comprises the ability to either manually pre-populate a set of nodes or automatically create a set of nodes for the new decision tree. In embodiments, the new decision tree may be associated with a particular business-specific data repository. Embodiments disclosed herein include receiving an input and associating a set of inputs to one or more nodes in the new decision tree. The new decision tree may be based upon a template created by a user.

Through use of machine learning and deep neural networks (and sharing of information contained therein), rules and methodologies may be better refined and adapted to suit a particular user's needs. Booth usage analytics may also be reported to an administrator. More specifically, data and analytics associated with the booth may be shared as an analytics service to provide insight to usage of the booth, as well as other environmental data captured inside and outside of the booth, such as noise levels, light, temperature, power usage, and foot traffic around the booth.

The Smartbooth 102 may be configured to provide, internal or external to the Smartbooth, one or more highly-targeted advertisements. In certain embodiments, the advertisements may be determined through use of the adaptive and machine learning engines described above, and may further comprise one or more algorithms that are optimized in response to anonymized user profiles generated from data collected by one or more Smartbooths. For example, distinct user records may be created and collected via mobile app usage and multiple swipe-to-use sessions initiated on the same credit card, and data derived therefrom employed to determine the content of specific visual or other advertisements.

In some preferred embodiments, the Smartbooth 102 can activate an active privacy mode, where all sensors, cameras, and microphones are disconnected, thus creating a guarantee of privacy, either through deleting any monitoring data or through complete disconnection so that there is no monitoring of any sort. The privacy of a user can also be verified through third party verification, physical evidence or transparent disclosure of methods to maintain and guarantee privacy. Included in these embodiments, the Smartbooth 102 also has the ability to communicate with another individual in a different Smartbooth 102 located in a separate physical location. The audio, video, text, or file transfer between two Smartbooths 102 in two locations may be encrypted, run through a Virtual Private Network (VPN), and are not surveilled or monitored. While not in active privacy mode, encryption and VPN services may be used as the default mode.

Methods of Use

Figure 13:
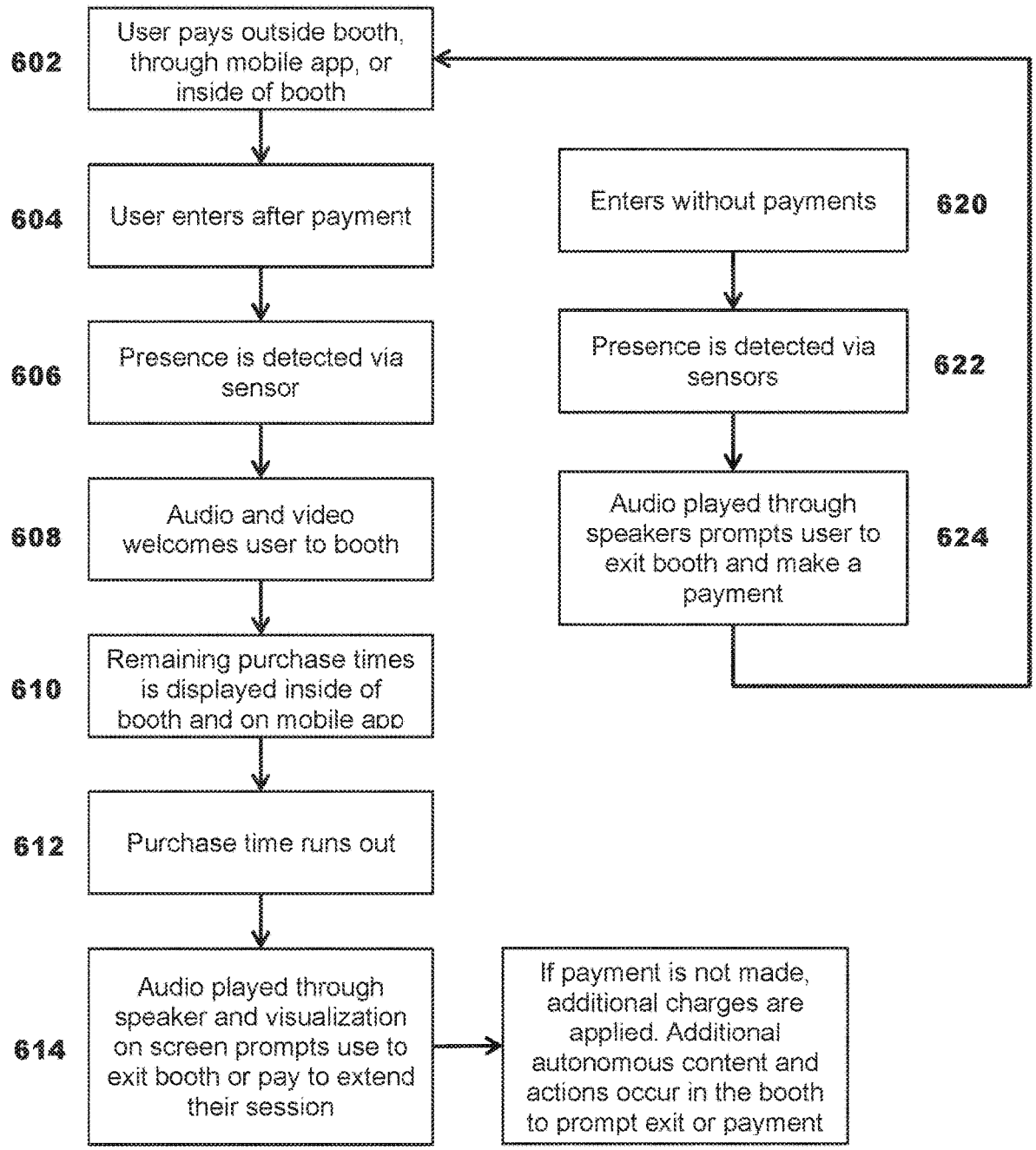
FIG. 13 illustrates a method of use according to embodiments of the present disclosure.

Referring now to FIG. 13, the present invention also discloses a method to use the Smartbooth 102 where, in one embodiment, a user pays for a session in the Smartbooth outside or inside the Smartbooth 602. The user then enters the Smartbooth after payment has been accepted 604, and the user's presence inside the booth is detected by the sensors inside the Smartbooth 606. Audio and/or video and/or text may be displayed/played through the Smartbooth speakers or displays to welcome the user to the Smartbooth session 608. Throughout the session, the remaining purchased time is displayed on the inside of the booth 610, and the Smartbooth displays also alert a user when the purchased time has run out 612. At the end of the user's session in the Smartbooth, audio is played through speakers to prompt the user to exit the booth or pay to extend the session 624. Visual messaging via text on screen or monitor will also be redundant to audio to communicate with redundancy or to hearing impaired users. It is to be understood that the sequence of these method steps is not critical for the method described herein, and may be arranged in a different order depending on the particular administrator or user of the Smartbooth 102.

In other embodiments, if a user enters the Smartbooth without making a payment 620, the user's presence inside the Smartbooth is detected 622, and audio is played through speakers inside the Smartbooth that prompts the user to exit the booth or to make a payment 624. Visual signals and/or text on a screen will also indicate to the user to exit the Smartbooth. Flickering lighting or other controls (like ventilation) may also be used to encourage a prompt exit once a session has expired. In other embodiments, an administrator and or local authorities will be alerted when an occupant remains in the Smartbooth and there is insufficient payment or funds. In such embodiment, the administrator will initiate an audio and or video conference and communication with the occupant of the Smartbooth.

The Smartbooth preferably guides first-time users through an on-boarding and account creation process, which then allows for the Smartbooth to recognize repeat users in subsequent sessions, as well as gather data such as user preferences including but not limited to lighting, content, olfactory, purchasing, and any other configurable or predictive needs or behaviors with and/or around a Smartbooth setting.

In the foregoing description, for the purposes of illustration, systems and methods were described in a particular order. It should be appreciated that in alternate embodiments, the methods may be performed in a different order than that described. It should also be appreciated that the methods described above may be performed by hardware components or may be embodied in sequences of executable instructions on machine-readable media, and which cause a machine, such as a general-purpose or special-purpose processor or logic circuits programmed with the instructions to perform the methods. These machine-executable instructions may be stored on one or more machine-readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Specific details were given in the description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine-readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted by any suitable means including memory sharing, message passing, token passing, network transmission, etc.

While illustrative embodiments of the invention have been described in detail herein, it is to be understood that the inventive concepts may be otherwise variously embodied and employed, and that the appended claims are intended to be construed to include such variations, except as limited by the prior art.

Moreover, though the present disclosure has included description of one or more embodiments and certain variations and modifications, other variations and modifications are within the scope of the disclosure, e.g. the use of a certain component described above alone or in conjunction with other components may comprise a system, while in other aspects the system may be the combination of all of the components described herein, and in different order than that employed for the purpose of communicating the novel aspects of the present disclosure. Other variations and modifications may be within the skill and knowledge of those in the art, after understanding the present disclosure. This method of disclosure is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A system for conducting private activities, comprising:
   an enclosed structure that creates an environment that allows a user to reserve and confirm the session in advance, the enclosed structure having a door associated with an accelerometer configured to track the state of the door being open, closed, or partially opened or closed, wherein:
   the system provides a secure and personalized internal environment, access to furniture, electronic power sources, display screens, and selective network connectivity;
   wherein the enclosed structure is locked after the user has vacated, and further comprising a disinfecting system that exposes the interior of the enclosed structure to a mist of disinfectant, a disinfecting environment, air that includes a disinfectant, ultra-violet radiation, a vacuum, or an inert gas for a predetermined amount of time;
   wherein the enclosed structure provides dynamic pricing blocks to the user and collects and validates user payment associated with use of the enclosed structure; and
   wherein the enclosed structure traffics media and advertisements that is provided on the display.

2. The system of claim 1, wherein the disinfecting system initiates automatically after the enclosed structure is locked.

3. The system of claim 1, further comprising a sensor that monitors the air within the enclosed structure to verify an absence of pathogen or to identify a number of pathogens present.

4. The system of claim 3, wherein the enclosed structure remains locked until the number of pathogens present in the air is below a predetermined level.

5. The system of claim 1, further comprising a series of sensors to determine whether the user has entered the enclosed structure, and further configured to prompt the user to commence a session.

6. The system of claim 5, wherein the series of sensors are pressure sensors.

7. The system of claim 5, wherein the series of sensors are force sensors.

8. The system of claim 5, wherein the series of sensors are located beneath the floor of the enclosed structure.

9. A system for conducting private activities, comprising:
   an enclosed structure that creates an environment that allows a user to reserve, customize, and confirm a session in advance, the enclosed structure comprising a ceiling, a floor, a plurality of walls interconnecting the ceiling to the floor, and a door in one wall that selectively provides access to an internal volume of the enclosed structure;

wherein the enclosed structure includes: a desk, a chair, an electronic power source, a display screen, and selective network connectivity;

an accelerometer configured to track the state of the door being open, closed, or partially opened or closed;

a liquid sensor associated with at least one of the desk, the chair, the electronic power source, and the display screen;

wherein the enclosed structure is locked after the user has vacated, and further comprising a disinfecting system that exposes the interior of the enclosed structure to a mist of disinfectant, a disinfecting environment, air that includes a disinfectant, ultra-violet radiation, a vacuum, or an inert gas for a predetermined amount of time;

wherein the enclosed structure provides dynamic pricing blocks to the user and collects and validates user payment associated with use of the enclosed structure; and wherein the enclosed structure traffics media and advertisements that is provided on the display.

10. The system of claim 9, further comprising a series of sensors associated with the floor configured to determine whether a user has entered the enclosed structure, and further comprising a speaker configured to prompt the user to commence the session.

11. The system of claim 9, wherein the desk includes a channel for routing liquid to the exterior of the enclosure or into a bladder.

12. The system of claim 9, wherein at least a portion of one wall of the plurality thereof is comprised of glass capable of selective opacity changes.

13. The system of claim 9, further comprising a decibel meter configured to compare noise levels at predetermined time intervals.

14. An enclosure for conducting private activities, comprising:

an enclosed structure that creates an environment that allows a user to reserve, customize, and confirm a session in advance, the enclosed structure comprising a ceiling, a floor, a plurality of walls interconnecting the ceiling to the floor, and a door in one wall that selectively provides access to an internal volume of the enclosed structure;

wherein the enclosed structure includes: a desk, a chair, an electronic power source, a display screen, and selective network connectivity;

an accelerometer configured to track the state of the door being open, closed, or partially opened or closed;

a liquid sensor associated with at least one of the desk, the chair, the electronic power source, and the display screen;

a series of sensors associated with the floor configured to determine whether a user has entered the enclosed structure, and further comprising a speaker configured to prompt the user to commence the session;

a decibel meter configured to compare noise levels at predetermined time intervals;

an advertising display associated with a wall of the plurality thereof, and a sensor that monitors foot traffic outside the enclosure;

wherein the desk includes a channel for routing liquid to the exterior of the enclosure or into a bladder;

wherein at least a portion of one wall of the plurality thereof is comprised of glass capable of selective opacity changes;

wherein the enclosed structure is locked after the user has vacated, and further comprising a disinfecting system that exposes the interior of the enclosed structure to a mist of disinfectant, a disinfecting environment, air that includes a disinfectant, ultra-violet radiation, a vacuum, or an inert gas for a predetermined amount of time;

wherein the enclosed structure provides dynamic pricing blocks to the user and collects and validates user payment associated with use of the enclosed structure; and wherein the enclosed structure traffics media and advertisements that is provided on the display.

* * * * *